United States Patent
Mann

(10) Patent No.: US 6,399,570 B1
(45) Date of Patent: Jun. 4, 2002

(54) ANTIMICROBIAL/ENDOTOXIN NEUTRALIZING POLYPEPTIDE

(75) Inventor: David M. Mann, Gaithersburg, MD (US)

(73) Assignee: Agennix, Inc., Houston, TX (US)

( * ) Notice: Subject to any disclaimer, the term of this patent is extended or adjusted under 35 U.S.C. 154(b) by 0 days.

(21) Appl. No.: 09/245,527

(22) Filed: Feb. 5, 1999

(51) Int. Cl.$^7$ .......................... A61K 38/00; A61K 38/16
(52) U.S. Cl. .............................. 514/12; 514/8; 514/12; 530/324; 530/300
(58) Field of Search .......................... 424/184.1, 185.1, 424/192.1, 194.1; 514/2, 8, 12; 530/395, 300, 324

(56) References Cited

U.S. PATENT DOCUMENTS

| | | | |
|---|---|---|---|
| 5,214,028 A | 5/1993 | Tomita et al. | 514/6 |
| 5,304,633 A | 4/1994 | Tomita et al. | 530/326 |
| 5,317,084 A | 5/1994 | Tomita et al. | 530/324 |
| 5,656,591 A | 8/1997 | Tomita et al. | 514/6 |
| 5,849,881 A | * 12/1998 | Connelely et al. | 530/400 |
| 5,849,885 A | * 12/1998 | Nuyens et al. | 530/416 |
| 6,060,058 A | * 5/2000 | Schryvers | 424/184.1 |
| 6,111,081 A | * 8/2000 | Conneely et al. | 530/400 |

FOREIGN PATENT DOCUMENTS

| | | |
|---|---|---|
| JP | 7(1995)-69915 | 3/1995 |
| JP | 8 (1996)-73499 | 3/1996 |
| WO | WO 91 13629 | 9/1991 |
| WO | WO 95 19372 | 7/1995 |
| WO | WO 96 06860 | 3/1996 |
| WO | WO 99 14231 | 3/1999 |

OTHER PUBLICATIONS

Orten, James M and Neuhaus, Otto W. Boichemistry, 8th ed. CV Mosby Co. 1970.*
Mann et al. Journal of Biological Chemistry 269(38):23661–23776, 1994.*
Legrand et al. Biochemical Journal 327(3):841–846, 1997.*
Mann, David M. Generation of Antibiotic Polypeptide from Lactoferrin. Dialog Report. 1999.*
Duvick, JP et al, Journal of Biol. Chem. vol. 267, p. 18814–18820, 1992 "Purification and characterization of a novel anti–microbial peptide from maize (Zae mays L.) kernels." (Sequence alignment only).*
Sanchez et al., Arch. Dis. Child. 67: 657–61 (1992).
Levay and Viljoen, Haematologica 80: 252–67 (1995).
Lönnerdal and Iyer, Annu. Rev. Nutr. 15: 93–110 (1995).
Database WPI, Section Ch, Week 199635, Derwent Pub. Ltd., London, GB; Class B04, AN 1996–350155 XP002145478 & JP 08 165248 A (Kuriiwa N), Jun. 25, 1996 abstract.
Ellison, R.T., Adv. Exp. Med. Biol. 357: 71–90 (1994).

(List continued on next page.)

Primary Examiner—Lynette R. F. Smith
Assistant Examiner—Ginny Allen Portner
(74) Attorney, Agent, or Firm—Albert P. Halluin; Karen K. Wong; Howrey, Simon, Arnold & White

(57) ABSTRACT

Disclosed is a 6 kDa host-defense polypeptide which is generated by proteolytic digestion of the lactoferrin molecule. The 6 kDa host-defense polypeptide has antimicrobial activity and also endotoxin-neutralizing activity. Also disclosed are functional variants of the 6 kDa host defense polypeptide, which include N-terminal and C-terminal truncations of the 6 kDa polypeptide, and other modifications of the polypeptide, such as amino acid substitutions which preserve or enhance activity.

17 Claims, 10 Drawing Sheets

OTHER PUBLICATIONS

Appelmelk et al., *Infect. Immun.* 62: 2628–2632 (1994).
Elass–Rochard et al., *Biochem. J.* 312: 839–845 (1995).
Bellamy et al., *Biochimica et Biophysica Acta 1121*: 130–136 (1992).
Bever et al., *Inflammation 13*: 309–16 (1989).
Levy et al., *Infect. Immun.* 57: 1632–4 (1989).
Boman et al., Eds., Antimicrobial Peptides, John Wiley & Sons Ltd., New York, NY (1994).
Hoffmann et al., *Curr. Opin. Immunol.* 8: 8–13 (1996).
Martin et al., *J. Leukoc. Biol.* 58: 128–36 (1995).
Ganz et al., *Curr. Opin. Hematol.* 4: 53–8 (1997).
Tang and Wong, *J. Cell Biochem.* 33: 53–63 (1987).
Briozzo et al., *Cancer Research* 48: 3688–3692 (1988).
Bazin et al., Inflammation, Biochemistry and Drug Interaction, A. Bertelli and J.C. Houck, Eds., Excerpta Medica., Amsterdam 1969), pp. 21–28.
Greenbaum, L.M., Proteases and Biological Control, E. Reich, D.B. Rifkin and E. Shaw, Eds. (Cold Spring Harbor Laboratory, New York, 1975), pp. 223–228.

\* cited by examiner

FIG. 1

ANTIMICROBIAL/ENDOTOXIN NEUTRALIZING POLYPEPTIDE

BACKGROUND OF THE INVENTION

Although humans are at continuous risk of infection by microbial pathogens, most survive these repeated onslaughts by mounting rapid responses that utilize a variety of antimicrobial proteins and small polypeptides. This branch of the human innate immune system represents a more fundamental host defense mechanism than the slower acting clonal systems since antimicrobial polypeptides are also used by primitive animals, insects, and even plants (H. G. Boman, J. Marsh and J. A. Goode, Eds., *Antimicrobial Peptides*, (John Wiley & Sons Ltd., New York, N.Y., 1994); Hoffmann et al., *Curr. Opin. Immunol.* 8: 8–13 (1996)).

In addition to inhibiting the growth of microbial pathogens, the immune system also neutralizes a variety of toxins produced by invading microbes. One particularly toxic product, produced by Gram-negative bacteria, is endotoxin. Endotoxin (lipopolysaccharide; LPS) is a constitutive component of the outer membrane of Gram-negative bacteria and is released when the bacteria die or multiply (Rietschel et al., *Immunobiology.* 187: 169–190 (1993)). It is estimated that approximately 400,000 patients annually in the United States present with bacterial sepsis, of which 100,000 ultimately die of septic shock and about half of these cases are caused by Gram-negative bacteria (Parrillo, J. E., Shock syndromes related to sepsis. In Cecil Textbook of Medicine (20th edition). J. C. Bennett and F. Plum, editors. W. B. Saunders Company, Philadelphia. 496–501 (1996)). Gram-negative sepsis and septic shock primarily results from endotoxin-induced excessive production and release of inflammatory cytokines by cells of the immune system, particularly macrophages (Beutler, B., and A. Cerami, *Annu. Rev. Biochem.* 57: 505–518 (1988); Rosenstreich, D. L., and S. Vogel, Central role of macrophages in the host response to endotoxin. p. 11–15. In D. Schlessinger (ed.), Microbiology. American Society for Microbiology. Washington, D.C. (1980)). TNF-α is the primary mediator of the systemic toxicity of endotoxin (Beutler, B., and A. Cerami, *Annu. Rev. Biochem.* 57: 505–518 (1988); Heumann et al., *J. Endotoxin Res.* 3: 87–92 (1996)).

Lipid A is the toxic portion of endotoxin (Rietschel et al., *Immunobiology.* 187: 169–190 (1993)). Monoclonal anti-lipid A antibodies have been tested for treating Gram-negative sepsis and septic shock, but their clinical efficacy has not been demonstrated consistently (Verhoef et al., *J. Antimicrob. Chemother.* 38: 167–182 (1996)), probably due to their poor ability to bind and neutralize endotoxin (Warren et al., *J. Exp. Med.* 177: 89–97 (1993)). Newer developments include identification of synthetic anti-endotoxin polypeptides mimicking polymyxin B (Rustici et al., *Science* 259: 361–365 (1993)) and a number of cationic anti-endotoxin polypeptides derived from host defense proteins. These include a recombinant 23 kDa fragment derived from bactericidal/permeability-increasing protein (Fisher et al., *Crit. Care Med.* 22: 553–558 (1994); Marra et al., *Crit. Care Med.* 22: 559–565 (1994)), a 28-mer peptide derived from bee melittin (Gough et al., *Infect. Immun.* 64: 4922–4927 (1996)), a 33-mer peptide derived from an 18 kDa cationic antibacterial protein (Larrick et al., *Infect. Immun.* 63: 1291–1297 (1995)), and synthetic polypeptides based on the crystal structure of Limulus anti-LPS factor (Reid et al., *J. Biol. Chem.* 271: 28120–28127 (1996)).

Lactoferrin (LF) is an 80 kDa iron-binding glycoprotein that is synthesized exclusively by neutrophils and mucosal epithelium and released extracellularly upon their activation by inflammatory stimuli (Sanchez et al., *Arch. Dis. Child.* 67: 657–61 (1992); P. F. Levay and M. Viljoen, *Haematologica* 80: 252–67 (1995); B. Lonnerdal and S. Iyer, *Annu. Rev. Nutr.* 15: 93–110 (1995); R. T. Ellison, *Adv. Exp. Med. Biol.* 357: 71–90 (1994)). It is thought to be a mammalian host defense protein whose mechanism of protection is poorly understood. In vivo LF provides an antibacterial prophylactic effect (Trumpler et al., *Eur. J. Clin. Microbiol. Infect. Dis.* 8: 310–3 (1989)). LF treatment in vivo has been reported to lower the incidence of Gram-negative bacteremia (Trumpler et al., *Eur. J. Clin. Microbiol. Infect. Dis.* 8: 310–313 (1989)). In vitro it has been shown to inhibit the growth of a variety of microbes by chelating iron (J. D. Oram and B. Reiter, *Biochim. Biophys. Acta* 170: 351–65 (1968); A. Bezkorovainy, *Adv. Exp. Med. Biol.* 135: 139–54 (1981)).

LF contains a strongly basic region close to its N-terminus and binds to a variety of anionic biological molecules including lipid A (Appelmelk et al., *Infect. Immun.* 62: 2628–2632 (1994)) and glycosaminoglycans which occur on the surface of most cells and in most extracellular matrices (Mann et al., *J. Biol. Chem.* 269: 23661–7 (1994)). Lactoferricin H (residues 1–47) and lactoferricin B (residue 17–41) are released by pepsinolysis of human or bovine LF, respectively, and may have more potent antibacterial activity than the native proteins (Bellamy et al., *Biochim. Biophys. Acta.* 1121: 130–136 (1992)). A region composed of residues 28–34 is reported to contribute to the high affinity binding of human LF and lactoferricin H to endotoxin (Elass-Rochard et al., *Biochem. J.* 312: 839–845 (1995)). LF and lactoferricin B have been shown to inhibit the endotoxin-induced interleukin-6 response in human monocytic cells (Mattsby-Baltzer et al., *Pediatr. Res.* 40: 257–262 (1996)). Previously identified fragments of LF which exhibit antimicrobial activity were isolated from pepsin hydrolysates of LF (Tomita et al., (1993) U.S. Pat. No. 5,214,028; Tomita et al., (1994) U.S. Pat. No. 5,304,633; Tomita et al., (1994) U.S. Pat. No. 5,317,084; Tomita et al., (1997) U.S. Pat. No. 5,656,591).

Previous studies have established that the N-terminal 33 residues of human LF represent the minimal sequence that mediates binding of the protein to anionic polysaccharides such as glycosaminoglycans (Mann et al., *J. Biol. Chem.* 269: 23661–7 (1994)). This sequence contains a cationic head (residues 1–6) and tail (residues 28–33) which combine to form the glycosaminoglycan-binding site. However, these studies provided no evidence which indicated that this polypeptide had antimicrobial or endotoxin-neutralizing activity.

SUMMARY OF THE INVENTION

In one aspect, the present invention relates to a 6 kDa host-defense polypeptide which is generated by proteolytic digestion of the lactoferrin molecule. The 6 kDa host-defense polypeptide has antimicrobial activity and also endotoxin-neutralizing activity. The present invention also relates to functional variants of the 6 kDa host defense polypeptide, which include N-terminal and C-terminal truncations of the 6 kDa polypeptide, and other modifications of the polypeptide, such as amino acid substitutions which preserve or enhance the activity of the polypeptide.

In another aspect, the present invention relates to a therapeutic method for treating or preventing a disease resulting from a microbial infection of an individual comprising administering a therapeutic amount of the antimicrobial polypeptide or functional variant thereof to the individual. This method is useful in treating bacterial infections. This method can also be used to treat diseases which resulting from infections caused by a mycobacterium, such as tuberculosis or leprosy. This method is also useful in treating bacterial infections which cause bacterial sepsis in the infected individual. This method can also be used to treat infections caused by other microbes, such as fungal infections. The present invention can also be used to potentiate the therapeutic action of an antimicrobial drug in a patient, by administering the polypeptide of the present invention with the antimicrobial drug.

In another aspect, the present invention relates to a method for neutralizing circulating endotoxin in a patient by administering the endotoxin-neutralizing polypeptide or functional variant thereof of the present invention to the patient. Similar methods of use for the present invention include neutralizing endotoxin in a product by contacting the endotoxin with the endotoxin-neutralizing polypeptide or functional variant thereof of the present invention.

Also encompassed within the scope of the invention are methods for potentiating the endotoxin-neutralizing and antimicrobial activity of the polypeptide of the present invention. This can be done for example, by adjusting the ionic strength of the immediate environment. In addition, methods for increasing the in vivo production of the 6 kDa LF fragment in a patient by in vivo proteases are also disclosed. Such methods involve sensitizing LF to proteolysis and also increasing the activity of the proteases which generate the 6 kDa fragment from LF.

BRIEF DESCRIPTION OF THE FIGURES

FIG. 1 is a diagrammatic representation of the inhibition of *E. coli* growth by varying doses of a heparin-purified 6 kDa polypeptide generated from the N-terminus of human LF by cathepsin D (squares) or pepsin (circles). All points represent the average of triplicates and the standard deviation bars are smaller than the symbols.

DETAILED DESCRIPTION OF THE INVENTION

Figure 2:
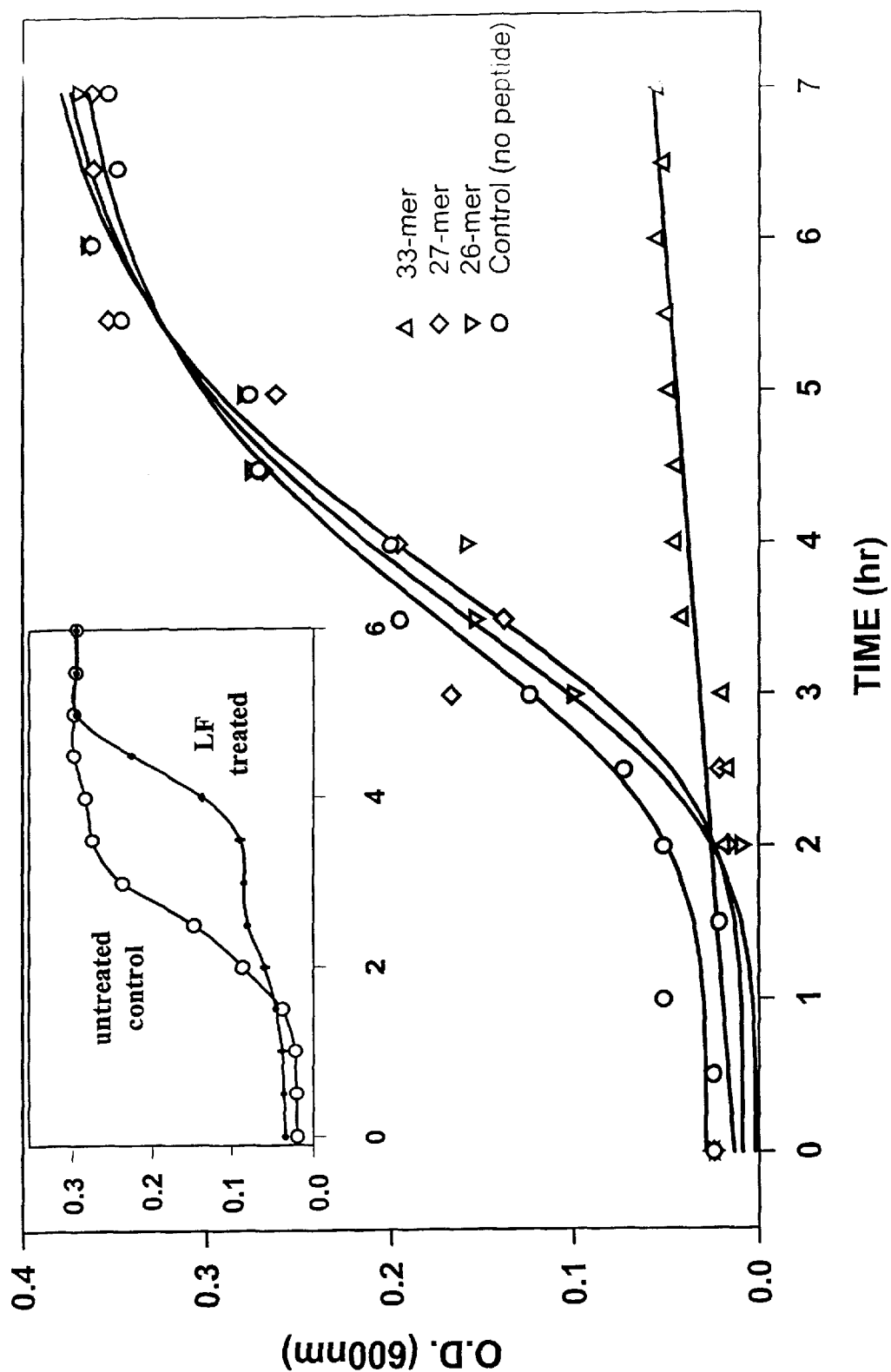
FIG. 2 is a growth curve of *E. coli* 0111 in the presence of 50 μM LF or the N-terminal 27-mer, 26-mer, 33-mer LF polypeptide fragments, over a 7 hour time course.

The present invention is based on the finding that a host-defense polypeptide generated from lactoferrin (LF) demonstrates significantly stronger anti-microbial and endotoxin-neutralizing activity than fragments of LF previously characterized. The host-defense polypeptide generated from LF also differs from the parent LF in the mechanism by which it inhibits microbial growth. While LF is thought to act by binding iron ions and temporarily starving microbes of this necessary ion, the 6 kDa polypeptide generated from LF acts through an iron-independent mechanism, by binding to the outer surface of the microbe and damaging the cell membrane to cause cell leakiness. The antimicrobial activity exhibited by the 6 kDa polypeptide is more stable (non-transient) than that exhibited by full length LF. The host-defense polypeptide is generated in vitro, and possibly in vivo, from the digestion of LF by cathepsin D. The product, an approximately 6 kDa polypeptide fragment, consists of the N-terminal 49 amino acids of LF with the amino acids joined to form a single contiguous amide linkage backbone. Of particular interest, the polypeptides of the present invention exhibit significantly higher activities under physiological conditions of pH and ionic strength than previously identified LF fragments generated from pepsin digestion (Bellamy et al., *Biochimica et Biophysica Acta* 1121: 130–136 (1992); Tomita et al., (1993) U.S. Pat. No. 5,214,028; Tomita et al., (1994) U.S. Pat. No. 5,304,633; Tomita et al., (1994) U.S. Pat. No. 5,317,084; Tomita et al., (1997) U.S. Pat. No. 5,656,591). One such pepsin generated fragment (Bellamy et al., *Biochimica et Biophysica Acta* 1121: 130–136 (1992)) is similar to the 6 kDa polypeptide fragment of the present invention in that it is comprised of amino acids 1–47 of LF. However, the polypeptide of the prior art has no amide bond between amino acid 11 and 12. Rather, the polypeptide fragments on either side of the break are held together by a disulfide bridge. The Experiments detailed in the Exemplification section which follows indicate that the single contiguous amide linkage backbone of the amino acids of the polypeptide of the present invention, confers a higher activity to the polypeptide and functional variants thereof.

The amino acid sequence of the 6 kDa polypeptide fragment produced by cathepsin D digestion of LF corresponds to amino acids 1–49 of SEQ ID NO: 2 (Table 1). Since polypeptides comprised of this sequence (or of functionally analogous sequences, described in greater detail below) produced by chemical synthesis also demonstrate comparable activities, the polypeptide of the present invention, and any functional variants thereof, may be generated and/or isolated by any means known in the art. The presence of internal disulfide bonds are unnecessary for the antimicrobial and endotoxin-neutralizing activities of the polypeptides claimed herein, as long as the amino acids of the polypeptide are joined by a single contiguous amide linkage backbone. Homologs of the host-defense polypeptides isolated from other animal species, and their functional variants, are predicted to have activities analogous to the human 6 kDa LF fragment, and are also encompassed by the present invention.

TABLE 1

Sequence ID numbers

SEQ ID NO: 1
GRRRRSVQWCAVSQPEATKCFQWQRNMRKVRGP
SEQ ID NO: 2
GRRRRRSVQWCAVSQPEATKCFQWQRNMRKVRGPPVSCIKRDSPIQCIQAIA
SEQ ID NO: 3
PVSCIKRDSPIQCIQAIA
SEQ ID NO: 4
GRRRRS
SEQ ID NO: 5
MRKVRG
SEQ ID NO: 6
VQWCAVSQPEATKCFQWQRNMKVRG

Sequence and functional analyses indicate that a polypeptide which encompasses the first 51 residues of the LF protein (the 6 kDa polypeptide with 2 additional amino acids of the LF sequence, on the C-terminus) demonstrates essentially the same activity as the 6 kDa polypeptide. The amino acid sequence of this slightly longer polypeptide is listed as amino acid 1–51 of in SEQ ID NO: 2. Experiments detailed in the Exemplification section which follows indicate that up to 17 amino acids of the C-terminus and up to 3 amino acids of the N-terminus of the 51 amino acid polypeptide can be eliminated without a complete loss of activity, both antimicrobial and endotoxin-neutralizing. In this respect, the present invention relates to an isolated polypeptide with a sequence corresponding to amino acids 1–51 of SEQ ID NO: 2, lacking up to 17 amino acids of the C-terminus, and up to 3 amino acids of the N-terminus. In preferred embodiments, no more than 5 residues are eliminated from the C-terminus.

Without being bound by theory, the two-fold activity of the polypeptide, a) antimicrobial, and b) endotoxin-neutralizing, arises from the interaction of specific regions of the polypeptide with different target molecules. The microbial growth is thought inhibited by a mechanism similar to other defensins; disrupting the membrane organization of the cell envelope of a microbe by interacting with different components of the microbial membrane. Microbial membranes are made up primarily of a bilayer of phospholipids, with the hydrophilic phosphate heads present on the outside of the bilayer, (e.g. the cell surface) and the hydrophobic lipid tails buried in the inner part of the bilayer. The polypeptide contains two clusters of basic residues separated by a stretch of amino acids which have a high content of hydrophobic residues. The combination of basic clusters separated by a more hydrophobic stretch enables the polypeptide of the present invention to interact with the hydrophilic membrane surface and also with the hydrophobic lipid tails within the bilayer. This combination of interactions leads to intercalation of the polypeptide into the membrane, which leads to membrane disruption. The biochemical components of the polypeptide which interact with the lipid bilayer components interact very similarly with lipopolysaccharides located on the bacterial surface, which have endotoxin activity, also comprised of a hydrophilic portion and a hydrophobic portion. Endotoxin, when present on the bacterial surface, is a component of a larger lipopolysaccharide (LPS) molecule. LPS, is a component of the outer membrane of all Gram-negative microbes. The hydrophilic component (polysaccharide), of LPS is located at the outer surface of the membrane, and the hydrophobic component (lipid A), is located in the inner part of the bilayer. The lipid A portion of the LPS molecule is the inflammatory or endotoxin portion of the LPS molecule. The clusters of basic residues are thought to bind to the negatively charged sites in the polysaccharide portion of LPS and on the most exposed head group of its lipid A tail, allowing the hydrophobic intervening region to bind to and neutralize the lipid A.

Figure 1:
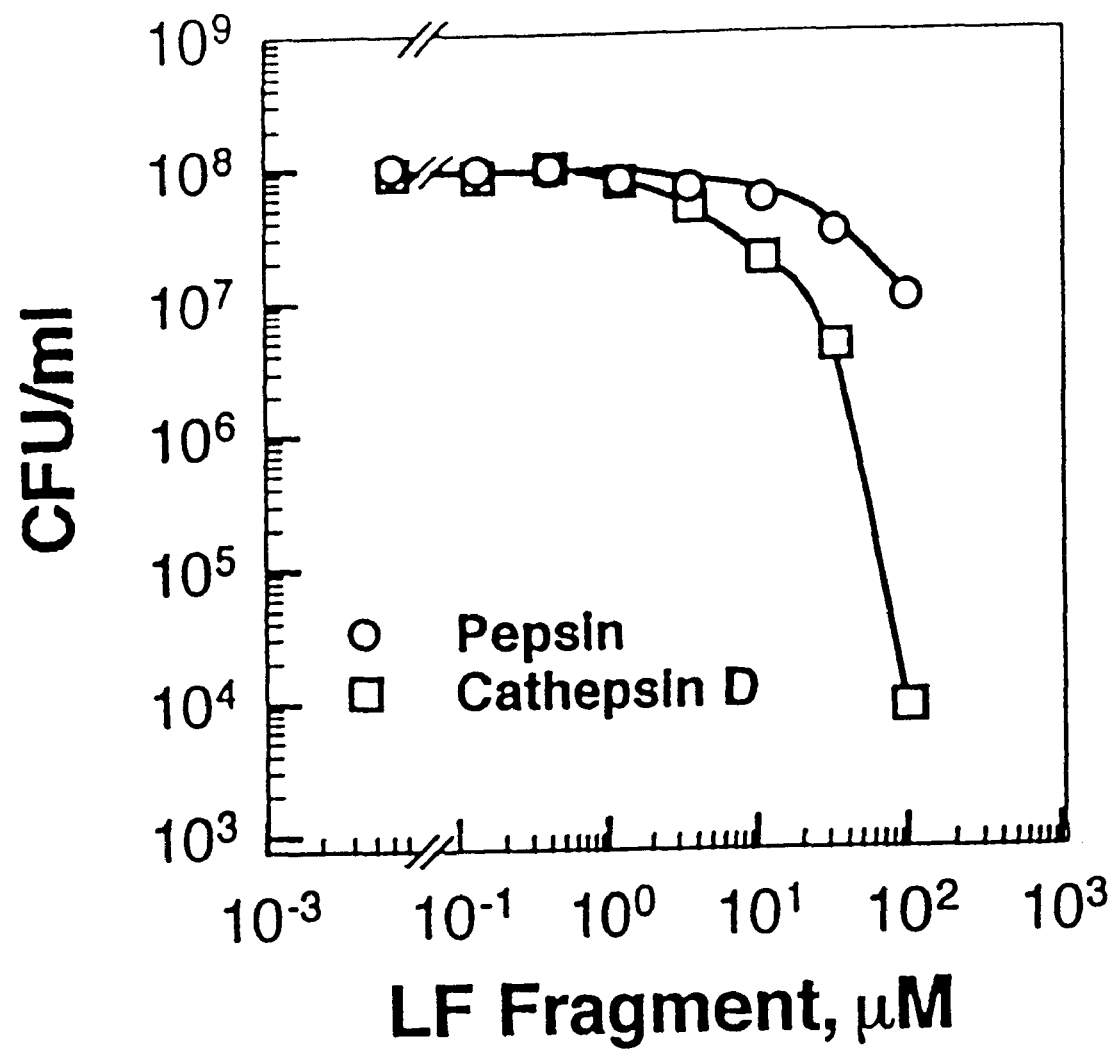

Under conditions which differ from those at the microbe surface, other types of binding may occur. Results presented in the Exemplification which follows indicate that a polypeptide which has the functional components described above, but contains only one functional basic cluster, for example LF-27, which has the amino acid sequence listed in SEQ ID NO: 6 (FIG. 1), has significant neutralizing activity towards endotoxin which is not in the context of the surface of the microbe (e.g. when it is shed from bacteria or extracted by preparative means as in foods or pharmaceuticals). In such circumstances, the lipid A portion of the molecule is more exposed and therefore the endotoxin is more accessible to the polypeptide. At high concentrations of polypeptide, or under abnormal salt conditions, or when the LPS is extracted or shed, or when disorganized while still in the outer membrane, the hydrophobic intervening region of the polypeptide can still mediate binding to LPS via lipid A, leading to the inactivation of the endotoxic effects of the lipid A portion of LPS.

One of skill in the art will recognize that amino acid substitutions, insertions or deletions of the 6 kDa LF polypeptide fragment sequence which preserve the biochemical properties of the molecule involved with these interactions preserve the antimicrobial and endotoxin-neutralizing activities in the resulting polypeptides. Polypeptides resulting from such amino acid substitutions, insertions or deletions are considered to be functional variants of the 6 kDa LF fragment, and as such are also encompassed within the scope of the present invention. As introduced above, specific regions of the LF fragment are involved in the antimicrobial and endotoxin-neutralizing activity. More specifically, these regions include two basic clusters, one located at the N-terminus and the other from residue 28 to 31, inclusively. In addition, the relative hydrophobicity of the amino acid sequences which flank these basic clusters also contribute to the activity of the polypeptide. The following formula defines the critical components of the 6 kDa polypeptide of the present invention and functional variants thereof:

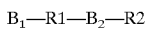

wherein $B_1$ and $B_2$ represent clusters of amino acids containing from 2–7 amino acids with at least 2 of the 2–7 amino acids being strongly basic, and R1 is between 17 and 21 amino acids having a grand average of hydropathicity value (GRAVY) (J. Kyte and Doolite, R. F., *J. Mol. Biol.* 157: 105–132 (1982)) of at least −0.609 and an aliphatic index value (A. Ikai, *J. Biochem.* 88: 1895–1898 (1980)) of at least 35.45, and R2 is between 1 and 17 amino acids and has a GRAVY value of at least 0.174 and an aliphatic index value of at least 97.14, the amino acids of the polypeptide being joined to form a single contiguous amide linkage backbone.

The amino acids lysine, arginine, histidine and any amino acid variant that is synthesized or chemically modified such that it has a positively charged group on its side chain, qualify as strongly basic amino acids in the context of this description and other definitions of the present invention, presented below.

Aliphatic index is calculated according to the following formula: aliphatic index=X(Ala)+a·X(Val)+b·(X(Ile)+X(Leu)) where X(Ala), X(Val), X(Ile), and X(Leu) are mole percent (100 X mole fraction) of alanine, valine, isoleucine, and leucine. a and b are the relative volume of valine side chain (a=2.9) and of Leu/Ile side chains (b=3.9) to the side chain of alanine.

In preferred embodiments, R1 and R2 of the isolated polypeptide have no more than 1 acidic amino acid each. Aspartic acid, glutamic acid, and an amino acid variant which is synthesized or chemically modified such that it has a negatively charged group on its side chain, qualify as acidic amino acids in the context of this description and other definitions of the present invention presented below. In one embodiment, R2 of the isolated polypeptide is PVSCIKRDSPIQCIQAIA (SEQ ID NO: 3). Alternatively, R2 can be a C-terminal truncation of this sequence (SEQ ID NO: 3). In another embodiment, $B_1$ of the isolated polypeptide is GRRRRS (SEQ ID NO: 4) or a truncation thereof, which retains at least two consecutive R's in the sequence. Some examples of $B_1$ produced by such a truncation are GRR, RRS, RRR, and RR. In another embodiment, $B_2$ of the isolated polypeptide is MRKVRG (SEQ ID NO: 5).

In a preferred embodiment, the isolated polypeptide has the sequence of amino acids 1–51 listed in SEQ ID NO: 2. In an alternate embodiment, the isolated polypeptide comprises this sequence with an amino acid substitution at position 16, the substitution decreasing the relative hydrophilicity of the polypeptide region in which it lies, thereby increasing the relative hydrophobicity of that region. Increasing the hydrophobicity of this region of the molecule is likely to potentiate the antimicrobial and the endotoxin-neutralizing activity of the polypeptide. One example of such a substitution is a neutral charge amino acid substitution at position 16, for example glycine. A neutral charge amino acid is defined as an amino acid which has no net charge when it occurs within the context of a polypeptide, at physiological pH. Another example of such a substitution is with a non-charged hydrophobic amino acid, such as valine or alanine. It should be noted that similar substitutions as those described directly above, at position 41 are expected to have the same overall potentiating effect. These types of amino acid substitutions made in functional variants of the polypeptide are in turn expected to potentiate the activity of these variants.

Another aspect of the present invention is based upon the finding that the isolated polypeptide LF-33, a 33-mer which results from the elimination of the C-terminal 17 amino acids of the 6 kDa host-defense polypeptide, the amino acids being joined to form a single, contiguous amide linkage backbone, exhibits antimicrobial and endotoxin-neutralizing activity equivalent to that of the above described 6 kDa LF fragment. The amino acid sequence of LF-33 is listed in SEQ ID NO: 1 (Table 1).

LF-33 and LF-27 are specifically excluded from the polypeptide claims of the present invention in light of the fact that they have been previously disclosed as polypeptides which bind anionic polysaccharides such as glycosaminoglycans (Mann et al., *J. Biol. Chem.* 269: 23661–7 (1994)). However, LF-33 and LF-27 are not excluded from pharmaceutical compositions of polypeptides of the present invention, fusion protein claims, or methods claims of the present invention.

As with the 6 kDa LF fragment, polypeptides which result from amino acid substitutions, insertions or deletions of the LF-33 polypeptide sequence which preserve the biochemical properties of the molecule critical for activity, including the 2 basic clusters and the hydrophobicity of the intervening sequences, are functional variants of LF-33 in that they function via the same mechanisms and exhibit similar activities. The formula:

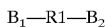

defines critical components of LF-33 and functional variants thereof, where $B_1$ and $B_2$ and R1 are described above.

In preferred embodiments, R1 of the isolated polypeptide has no more than 1 acidic amino acid, qualifying acidic amino acids being described above. In one embodiment, $B_1$ of the isolated polypeptide is GRRRRS (SEQ ID NO: 4) or a truncation thereof, which retains at least two consecutive R's in the sequence, examples given above. In another embodiment, $B_2$ of the isolated polypeptide is MRKVRG (SEQ ID NO: 5).

In another embodiment, the isolated polypeptide comprises the amino acid sequence listed in SEQ ID NO: 1 with an amino acid substitution at position 16, the substitution resulting in a decreased relative hydrophilicity of the polypeptide region in which it lies, thereby increasing the relative hydrophobicity of that region. This substitution is expected to potentiate the activity of the polypeptide. Similar substitutions made in other functional variants of the polypeptide are, in turn, expected to potentiate the activity of those variants. Examples of such substitutions are given above.

The antimicrobial and endotoxin-neutralizing polypeptide of the present invention can also be characterized by the presence of characteristic amino acids at specific positions within the polypeptide. Polypeptides with amino acid sequences which are analogous to amino acids 1–51 of SEQ ID NO: 2 and functional fragments thereof (in which up to 20 amino acids are deleted from the C-terminus) with regard to these specific positions are also functional variants, and as such are also encompassed by the present invention. More specifically the functional variant has a basic residue at positions 2, 3, 4, 5, 28, 29, 31, 39, and 40, and a hydrophobic residue at positions 7, 9, 10, 11, 12, 17, 18, 20, 21, 23, 32, 35, 37, 38, 44, 46, 47, 49, and 50, and an acidic residue at position 16 and 41. As described above, the amino acids of the antimicrobial polypeptide or functional variant are joined to form a single contiguous amide linkage backbone. Amino acids which qualify as basic residues and as acidic residues in this context are discussed above. In the context of this and other definitions or descriptions of present invention herein, hydrophobic residues include phenylalanine, leucine, isoleucine, tyrosine, tryptophan, valine, methionine, and proline. Alternatively, residues at position 10, 20, 37, and 46 can be cysteines, as in the wild type amino acid sequences of LF. In preferred embodiments, residues of the functional variant at non-specified positions are designated by the corresponding amino acids of the 51 amino acid polypeptide, listed in SEQ ID NO: 2, or are conservative substitutions of these residues.

An alternate embodiment of the present invention is the antimicrobial polypeptide or functional variant thereof described directly above which has a neutral charge amino acid substitution at position 16 and/or position 41. In preferred embodiments, a neutral charge amino acid with a hydrophobic side chain is substituted at position 16 and/or position 41. As discussed above, such analogous substitution are also expected to potentiate the activity of any functional variants in which they are made.

Experimental evidence indicates that the antimicrobial polypeptide comprised of amino acids 1–51 of SEQ ID NO: 2 maintains significant activity with up to 3 amino acids deleted from the N-terminus. Accordingly, functional variants of the antimicrobial polypeptide also include the above described functional variants with an additional 1–3 amino acids deleted from the N-terminus.

Another aspect of the present invention relates to a fusion protein that promotes rapid clearance of endotoxin from the body of an animal via an endocytosis clearance pathway. The fusion protein results from the fusion of a first polypeptide which is the endotoxin-neutralizing polypeptide of the present invention or a functional variant thereof, with a second polypeptide comprising a polypeptide sequence which is recognized and internalized by cells via an endocytosis clearance pathway. Suitable polypeptides for the first component of the fusion protein are described above. In a preferred embodiment, the first polypeptide component of the fusion protein is comprised of amino acids 1–51 of SEQ ID NO: 2.

The resulting fusion protein has the first polypeptide (the endotoxin-neutralizing fragment) N-terminal to the second polypeptide (the endocytosis clearance fragment) or alternatively, the second polypeptide N-terminal to the first polypeptide. The fusion protein retains the respective activities of the individual components. Some minor modifications (e.g. a linker region between the two polypeptide fragments) may be required to preserve these functions.

Other aspects of the present invention relate to methods of use of the polypeptide and functional variants thereof of the present invention. For brevity, the term polypeptides of the present invention is used herein to include both the original 6 kDa LF polypeptide fragment, and all functional variants described in detail above. As discussed above LF-33 and LF-27 are not excluded from the methods claims described herein.

Another aspect of the present invention is the method for inhibiting microbial growth. Polypeptides of the present invention can be used to inhibit microbial growth under various circumstances. For example, the polypeptides of the present invention can be administered therapeutically to treat or prevent disease in an individual resulting from a microbial infection.

A variety of microbial infections can be inhibited by treatment with the above described polypeptides. Experiments presented in the Exemplification section indicate that therapeutic administration of these polypeptides inhibits and can reverse the progression of a bacterial infection. Additional evidence indicates that some fungal infections can also be curtailed. Because the antimicrobial polypeptides of the present invention are thought to inhibit microbial growth by disrupting the cellular membrane of the microbe, any microbe which possesses such a cellular membrane is potentially susceptible to growth inhibition by the antimicrobial polypeptides. Viruses which contain lipid envelopes may also be susceptible to the antimicrobial effects of the polypeptides of the present invention.

In preferred embodiments, the microbial infection is a bacterial infection. This includes, without limitation, bacterial infections which are caused by mycobacteria. Mycobacteria are resistant to many antimicrobial drugs. Mycobacteria cause two of the most important diseases in history, tuberculosis and leprosy. Most cases of human tuberculosis are caused by *Mycobacterium tuberculosis,* but a significant number of cases are caused by *Mycobacterium bovis.* The development and spread of new resistant strains of bacteria, especially mycobacteria, are increasingly posing a public health threat. The antimicrobial polypeptides described above are useful in treating patients suffering from these resistant strains of microbes which currently threaten public health.

Many bacterial infections cause bacterial sepsis in the infected individual. Results detailed in the Exemplification section which follows indicate that the polypeptides described above also have endotoxin-neutralizing activity. Administration of these dual activity polypeptides to an individual suffering from a septic bacterial infection produces a significant therapeutic effect, by reducing both the sepsis caused by the infection, and the infection itself.

An individual suitable for treatment is any animal (mammal or otherwise) which is afflicted with or otherwise susceptible to one or more of the above described microbial infections. In a preferred embodiment, the individual is a human. In another embodiment, the individual is a livestock animal. In another embodiment, the animal is a show animal or a household pet.

Administration of the polypeptide to the individual is either systemic or localized, and is largely determined by the specific infection being treated. Systemic administration can be accomplished by several routes, including but not limited to intravenous administration, inhalation, and ingestion. Localized administration can be topical or internal. Such administration can be accomplished by several routes, including, but not limited to, subcutaneous, dermal, intradermal, and intraperitoneal administration, inhalation, and ingestion.

It will often be of use to administer a formulation of the polypeptides of the present invention which includes a pharmaceutically acceptable carrier. Possible formulations for therapeutic administration include a variety of pharmaceutical compositions, the appropriate use of which will depend upon the route of administration deemed necessary for treatment. Some useful formulations for topical administration are, for example, eyedrops, eardrops, or gingival applications, (e.g. drops, mouthwash, cream, or paste). The regimen of administration (e.g. route, dose, and course) which is therapeutic to the patient will vary with the individual to be treated (e.g. health, weight, metabolism), the site of infection, and the infecting pathogen. A therapeutic regimen should be developed by extrapolation from treatment with similar therapeutics in combination with empirical observation. Administration of the polypeptides of the present invention to prevent a microbial infection in an individual parallel the above described methods.

Another aspect of the present invention is based on the finding that the polypeptides of the present invention also exhibit activity at potentiating the therapeutic action of other antimicrobial drugs or agents. Experiments detailed in the Exemplification section show that co-administration of other antimicrobial agents with the antimicrobial polypeptides of the present invention, produce a synergistic antibiotic effect. These results indicate that the polypeptides of the present invention significantly increase the antibiotic activity of rifampicin or isoniazid. Without being bound by theory, this is thought to occur because the polypeptides of the present invention disrupt the integrity of the bacterial membranes, and this disruption results in a higher concentration of the antibiotic within the individual bacterium.

These results indicate that the polypeptides of the present invention can be therapeutically utilized to potentiate the activity of various antimicrobial agents or drugs. Co-administration of the polypeptides of the present invention with an antimicrobial agent enables therapeutic treatment of a patient with lower doses of the antimicrobial agent. Lower doses are preferable in situations such as when treating with an expensive drug, or one that produces undesired side effects, or one whose short half-life in vivo would otherwise rapidly reduce its concentration below that which is required for it to be efficacious. In addition, co-administration with antimicrobial agents or drugs may also allow for a shorter therapy period and/or the reversal of resistant phenotypes. Without limitation, microbes which resist an antimicrobial drug by decreasing their internal drug concentration (e.g. with decreased membrane permeability or increased cellular export or metabolism of the drug) are expected to be especially susceptible to the potentiating activity of these polypeptides.

The polypeptides of the present invention can be used to potentiate any antimicrobial agent or drug whose activity requires entry beyond the outer most surface of the microbe. In preferred embodiments, the antimicrobial drug is an antibiotic and the microbial infection is a bacterial infection. The causative agent is either a bacterium which is susceptible to the antibiotic, or alternatively is resistant to the antibiotic in the absence of antibiotic potentiation. In a preferred embodiment, the antibiotic is rifampicin or a structurally related molecule. In another embodiment, the antibiotic is isoniazid or a structurally related molecule. In another embodiment, the antimicrobial drug is an antifungal agent and the infection is a fungal infection. Patients include any individual (animal, mammal, human, etc.) which suffers from or is at risk of contracting an infection by a susceptible microbe.

The regimen of administration of the antimicrobial drug and the isolated polypeptide or functional variant of the present invention varies with the patient and the particular infection, and can be determined by one of skill in the art on a case by case basis. Formulations of the polypeptide will depend upon the regimen of administration, examples described above.

Another aspect of the present invention relates to the use of the above described polypeptides to neutralize endotoxin. The polypeptides of the present invention have endotoxin-neutralizing activity and can be used to neutralize endotoxin within the body of an individual (e.g. circulating in the bloodstream). The endotoxin may result from a pathogen which has infected the body, or alteratively, from a contaminant to which the body has been exposed (e.g. endotoxin contaminated blood, or other bodily fluid, tissue, or bodily surface). The polypeptides of the present invention are administered to the individual in a fashion similar to their administration for the treatment of a patient with a microbial infection, described above. The therapeutic regimen of administration of the polypeptides will vary with each case and can be developed by extrapolation from treatment with similar therapeutics in combination with empirical observation. Similar formulations to those described above for treatment of a microbial infection, can also be utilized in this method. Regimens of administration and useful formulations are also previously described in this document.

Alternatively, endotoxin in a patient can be neutralized by administration of a fusion protein comprised of a polypeptide with endotoxin-neutralizing activity fused with a polypeptide comprised of a polypeptide sequence which is recognized and internalized by cells via an endocytosis clearance pathway. The fusion protein to be administered is described in detail above.

The polypeptides of the present invention can be used not only as pharmaceutical and neutraceutical agents but also as additives for any products such as foods and medicinal or non-medicinal products which are taken into the bodies or otherwise applied onto or contacted with the body surface of humans or other animals or fluids, organs, and cells derived therefrom. The neutralization and/or removal of endotoxin from potentially contaminated products is highly beneficial in circumstances where the endotoxin could potentially harm living organisms which come into contact, directly or indirectly, with that product.

To neutralize endotoxin and/or inhibit microbial growth in a product, the product is contacted with a polypeptide or functional variant described in detail above. Contact of the product and the polypeptide can be made in a variety of ways including, but not limited to, dipping, spraying, mixing, adsorbing against, and exposing to vapors, and will depend upon the properties of the specific product.

The present method is useful for treating a variety of products. Biological products, defined herein as products which are derived from biological organisms or processes, are particularly at risk for contamination with microorganisms and endotoxin. Examples of biological products include without limitation, food products, tissue, living cells, products derived from living cells, blood or components thereof, as any other bodily fluid, drugs or other molecular preparations. Non-biological products, defined herein as a product not directly derived from a biological organism or process, for example glassware, surgical equipment, synthetic drugs or other molecular preparations, can also be treated. For effective use of the present invention, the product which is to be treated should not possess an activity which completely inactivates the endotoxin-neutralizing activity of all of the polypeptide quantity so applied. The polypeptides of the present invention can be added, assorted to, sprayed to, adhered to, coated onto, adsorbed to, chemically crosslinked to, or impregnated into any products which are generally desired to be prevented or inhibited from contamination by endotoxin or proliferating microorganisms. Alternatively, the polypeptide of the present invention can be immobilized on a surface over which a product is passed to remove endotoxin from or inhibit microbial growth in the product. A product which is treated with and retains endotoxin-neutralizing polypeptide can further be used to treat another product with which it is contacted.

Another aspect of the present invention is the induction of in vivo production of the LF host-defense polypeptide in an individual. Evidence presented in the Exemplification below indicates that the 6 kDa host-defense polypeptide fragment of LF is produced by digestion with the aspartic acid protease cathepsin D and that the sensitivity of LF to this digestion is increased upon exposure to polyanions. These findings indicate that administration of a polyanion (e.g. heparin, glycosaminoglycans, nucleic acids, or dextran sulfate) to a patient will increase the production of the 6 kDa polypeptide from LF (either endogenous LF or administered LF) by cathepsin D or a related enzyme. Alternatively, increasing the overall concentration or proteolytic activity of cathepsin D, or other proteases involved in the in vivo generation of the 6 kDa polypeptide will also increase the in vivo production of the polypeptide.

Other aspartic acid proteases which may also cleave the 6 kDa fragment from LF, include, without limitation cathepsin E, renin, and the aspartic protease of HIV. These proteases function optimally at pH 3.5–5. Adjusting the pH of the immediate environment of proteases involved in the generation of the 6 kDa polypeptide from LF, to optimal levels for protease activity, therefore will increase the in vivo production of the polypeptide from LF.

Another aspect of the present invention is the potentiation of the antimicrobial activity and endotoxin-neutralizing activity of the LF host-defense polypeptide and functional variants, by manipulation of the ionic strength of the immediate environment of the polypeptide. Because the activities of the polypeptides of the present invention are influenced by the ionic strength of the immediate environment, with sub-physiologic ionic strength being optimal, adjustments made to the immediate environment of the polypeptide will effect activity.

Results presented in the Exemplification section below indicate that the polypeptides of the present invention function to inhibit microbial growth at ionic strength less than 200 mM NaCl, with optimal activity observed at 50 mM NaCl (the lowest concentration tested). These results indicate that any treatment whereby the polypeptides of the present invention are exposed to an infectious microbe or endotoxin under conditions of reduced ionic strength, achieved for example by administering the polypeptide in sub-physiological ionic strength solutions or in combination with any agent that causes a dilution of salt concentrations of tissue fluids in the vicinity of the infection (such as a local acting diuretic), will significantly increase the potency of the polypeptide formulation. Along these lines, variants of the polypeptides can be designed to remain active at super-physiological ionic strengths. For example, by increasing the number of positively charged amino acids within one or both clusters of basic residues, or by decreasing the number of overall negatively charged residues within the polypeptide, one would predict that the salt inhibition of the variant polypeptides will be reduced.

Exemplification

In vivo Generation of the Host-defense Polypeptide from LF

LF is unusually resistant to proteolysis (R. D. Brines and J. H. Brock, *Biochim. Biophys. Acta* 759: 229–35 (1983)) and very little is known about its processing in vivo during inflammation. Inflamed human tissues were therefore examined for the presence of the N-terminal domain as a small (e.g. <12 kDa) polypeptide. Antibodies specific for the N-terminal 17 residues of mature human LF were used to probe immunoblots of sputum from an individual with a deep bronchial cough and purulent exudates ("pus") obtained from infected human skin. This identified the N-terminal domain of LF as present as a low molecular weight polypeptide (Mr~6,000–8,000) in all of the exudates tested. A scanning densitometric comparison of the immunostaining intensity of the sample 6 kDa polypeptide with that of the standard suggests this fragment was present in the exudates at 1–10 $\mu$M. The N-terminal polypeptide was also detected in human sputum, although it was not detected in gingival plaque or human saliva. In some of the tissue samples, polypeptides of intermediate size (e.g. 10–20 kDa) containing the N-terminal domain could be detected as minor components, likely resulting from incomplete processing of the liberated domain. These data provide the first direct evidence that the antimicrobial domain of LF is liberated in vivo during inflammatory events and that it remains intact as a small polypeptide within the tissue.

Activated Leukocytes Release the N-terminal 6 kDa Domain from LF

Since a hallmark of most microbial infections is infiltration by professional phagocytes, these cells were examined for the ability to liberate the antimicrobial domain from LF. Primary cocultures of monocytes and neutrophils were activated and examined for processing of the neutrophil-derived LF. Heparin-binding molecules were isolated from the combined cell extracts and culture releasate was obtained from primary human neutrophils and monocytes that were co-cultured and activated by FMLP. Immunoblotting of these with the anti-LF N-terminal polypeptide antibody detected a tightly spaced doublet of 6–8 kDa, corresponding to the antimicrobial domain, produced from neutrophil-derived LF by activated phagocytes. No immunoreactive polypeptide could be detected in neutrophils prior to activation, indicating that proteolytic liberation occurs subsequent to neutrophil degranulation. This confirmed that activated phagocytes liberate the N-terminal domain as a small polypeptide that retains heparin-binding function. Comparison of the intact LF obtained from equal numbers of neutrophils, revealed that a substantial proportion of the protein was processed by the activated co-cultures. Controls included the antibiotic domain released as a 6 kDa polypeptide from purified LF by pepsinolysis as well as the heparin-purified polypeptides from human colostrum. The N-terminal polypeptide was not detected in human colostrum, even though this contains very high concentrations of LF (~5–7 mg/ml) (Sanchez et al., *Arch. Dis. Child.* 67: 657–61 (1992)), indicating that it is not generated spontaneously. Rather, it is likely that this processing occurs in response to an inflammatory event.

Monocytes and neutrophils were cultured and activated separately to determine which type of phagocyte could liberate the N-terminal LF polypeptide. For these experiments, monocytes were supplemented with exogenously purified milk-LF (50 $\mu$g) since they had no endogenous LF. The culture medium was removed prior to extracting the cells with detergent and then heparin-binding molecules were isolated separately from both fractions and immunoblotted. The 6 kDa antimicrobial domain was detected in the culture media and cell extracts from both cell types. These results indicate that both cell types are capable of liberating the antimicrobial domain from LF. In both cultures, the antimicrobial domain was detected extracellularly as well as in the cell extract. Most of the fragment generated by the monocytes remained cell-associated rather than soluble whereas the opposite was true for neutrophils. The significance of this differential distribution between the extracellular and cellular compartments in the two cell types is consistent with a model in which neutrophil-released LF is cleaved extracellularly by neutrophil-derived proteases and intracellularly by mononuclear phagocytes, following its internalization by the latter (Britigan et al., *J. Immunol.* 147: 4271–7 (1991); Courtoy et al., *Lab. Invest.* 50: 329–34 (1984)) upon arrival at the site of inflammation. These studies demonstrate that professional phagocytes can liberate the antimicrobial domain from LF and could thus be responsible for generating the N-terminal polypeptide detected in infected tissues.

Release of a 6 kDa Polypeptide from LF by the Lysosomal Protease Cathepsin D To establish which protease(s) could be responsible for releasing the N-terminal domain, LF processing by several proteases relevant to inflammation or microbial infections, including elastase, cathepsins G and D, a matrix metalloproteinase, and the "V8" protease from *S. aureus*, was examined. Of these, only cathepsin D, a lysosomal protease abundant in phagocytes (Bever et al., *Inflammation* 13: 309–16 (1989); Levy et al., *Infect. Immun.* 57: 1632–4 (1989)), was able to liberate the N-terminus intact as a small, heparin-binding, polypeptide. Exposure of either iron-saturated or iron-free LF to even small amounts of cathepsin D ($1/200^{th}$, w:w) for a period as brief as five minutes yielded the N-terminal 6 kDa polypeptide, detectable by immunoblot analysis, using the N-terminal peptide-specific antibody. Increased accumulation of this polypeptide occurred with longer exposures to cathepsin D and the presence of polypeptide remained stable and resistant to further degradation for at least three days. N-terminal sequencing of the purified 6 kDa polypeptide revealed a single amino terminus corresponding to Gly-1 in the mature LF molecule. MALDI mass spectrometry analysis indicated a molecular mass of 5741 Da, very close to the value of 5744 Da expected for a LF polypeptide starting at Gly-1 and ending with Ala-49. Taken together, these results demonstrate that cathepsin D releases the N-terminal domain of LF as a polypeptide that, by virtue of its biochemical and structural similarities with other host defense polypeptides (H. G. Boman, J. Marsh, and J. A. Goode, Eds., *Antimicrobial Peptides*, (John Wiley & Sons Ltd., New York, N.Y. 1994); Hoffmann et al., *Curr. Opin. Immunol.* 8: 8–13 (1996); Martin et al., *J. Leukoc. Biol.* 58: 128–36 (1995); T. Ganz and R. I. Lehrer, *Curr. Opin. Hematol.* 4: 53–8 (1997)), is predicted to inhibit microbial growth.

Effect of pH on Liberation of 6 kDa LF Fragment by Cathepsin D

Cathepsin D is a major degradative protease found in the lysosomes of phagocytic and other cell types. It cleaves proteins that are endocytosed or phagocytosed by cells and subsequently delivered to the low pH lysosomal compartment of the cell. Like many lysosomal proteases, cathepsin D is proteolytically active with an acidic pH optimum (~pH 3.5) (Tang, J. and Wong, R. N. S., *J. Cell. Biochem.* 33: 53–63 (1987)), somewhat below that of the typical lysosome (pH~4.5–5.0) (Shoji Ohkuma and Brian Poole, *Proc. Natl. Acad. Sci.* 75: 3327–3331 (1978)). Experiments were performed which compare the liberation of the 6 kDa polypeptide from LF by cathepsin D at different pH.

Human LF purified from human milk was digested with cathepsin D at either pH 3.5, 4.0, 4.6, 5.0, or 7.4. Following digestion, the samples were electrophoreses by TRIS-glycine SDS-PAGE under non-reducing conditions. The fractionated products were then immunoblotted with a rabbit polyclonal antiserum which specifically recognizes only those polypeptides which contain the first 17 amino acids of the 6 kDa polypeptide. The analysis identified a band which migrated at approximately the same size as the 6 kDa polypeptide from the LF samples which had been incubated with cathepsin D at either pH 3.5, 4.0, 4.6 or 5.0. However, no 6 kDa product was detected from the pH 7.4 incubation. These results demonstrate that the release of the 6 kDa polypeptide is significantly increased at sub-physiological pH.

Binding of LF to Heparin Greatly Increases the Ability of Cathepsin D to Liberate the 6 kDa Fragment at Lysosomal pH One of the functions of polysaccharides is thought to be to confer proteins with resistance to attack by proteases. Since LF binds to anionic polysaccharides and this binding is mediated via its amino-terminal 33 residues (Mann et al., *J. Biol. Chem.* 269: 23661–23667 (1994)), experiments were performed to determine whether the polysaccharide heparin, a model polyanion which occurs naturally, protects LF from proteolysis by cathepsin D and reduces the liberation of the 6 kDa LF polypeptide.

LF was digested with cathepsin D at pH 5 for either 1 hr or 24 hrs either in the absence or presence of a ten fold molar excess of heparin. The products of the digest were fractionated under non-reducing conditions by SDS-PAGE and subjected to immunoblot analysis using an antibody specific for the first 17 residues of the LF protein as probe. Significantly higher amounts of the 6 kDa polypeptide were detected from the samples which included cathepsin D and heparin, versus the samples incubated in the absence of heparin. Similar immunoblot analysis of incubations of LF performed in the absence of cathepsin D or in the presence of pepstatin A, an inhibitor of cathepsin D, failed to identify a 6 kDa fragment. These controls indicated that the increased degradation was caused by cathepsin D, and was not due to a contaminating protease in the heparin preparations. These results demonstrated that the liberation of the 6 kDa polypeptide from LF by cathepsin D is increased dramatically in the presence of a polyanion such as heparin. This surprising result was the opposite of what was expected. The explanation for this result is not known, but it may relate to polyanions providing a micro-environment of low pH (due to their numerous acidic functional groups) which produces optimal conditions for aspartic acid proteases such as cathepsin D. These findings indicate that the release of the 6 kDa fragment from LF are likely facilitated in vivo by the presence of polyanions such as glycosaminoglycans or nucleic acids.

The 6 kDa LF Fragment Liberated by Cathepsin D is a More Potent Antimicrobial Agent than a Similar Fragment Liberated by Pepsin The antimicrobial activity of the catheptic polypeptide was measured against a clinical isolate, *E. coli* 0111. Microbial growth was inhibited at physiological ionic strength with a minimum inhibitory concentration (MIC) of ~1–5 $\mu$M polypeptide and a greater than 10,000-fold reduction in cell growth at 100 $\mu$M, where the number of viable CFUs was less than half of the original inoculum (from $2.14\times10^4$ to $8.8\times10^3$ CFU/ml) (FIG. 1). The 6 kDa catheptic fragment of LF is therefore at least as potent as twelve other natural antimicrobial polypeptides (H. G. Boman, J. Marsh, and J. A. Goode, Eds., *Antimicrobial Peptides*, (John Wiley & Sons Ltd., New York, N.Y., 1994)), and can function as a bactericidal agent. The antimicrobial fragment liberated by cathepsin D is ~10-fold more potent against bacteria than the one liberated by pepsin since the MIC for the latter was between 11–33 $\mu$M, a value in good agreement with the value of 18 $\mu$M previously reported for this pepsinolytic fragment (Bellamy et al., *Biochim. Biophys. Acta* 1121: 130–6 (1992)). At 100 $\mu$M polypeptide, the number of viable bacteria was more than 1,000-fold greater in the cultures treated with the pepsinolytic versus cathepsinolytic fragment (FIG. 1). The basis for this difference in potency may be related to the additional, internal, pepsin cleavages which occur between the two disulfide bridges in the 6 kDa domain (Mann et al., *J. Biol. Chem.* 269: 23661–7 (1994); Bellamy et al., *Biochim. Biophys. Acta* 1121: 130–6 (1992)).

The efficiency of cathepsin D in generating the antimicrobial polypeptide from LF is significant for several reasons. Although it is a member of the aspartic family of proteases that includes chymosin, renin, the HIV-1 protease, and pepsin (K. Takahashi, Ed., *Aspartic Proteinases: Structure, Function, Biology, and Biomedical Implications* (Plenum Press, New York, 1995)), and has similar structural features and pH requirements to pepsin, cathepsin D is distinct from these proteases in that it is generally found in the lysosomal compartment of all cells and abundant in professional phagocytes (J. Tang and R. N. S. Wong, *J. Cell. Biochem.* 33: 53–63 (1987)). Cathepsin D is also secreted from cells as an active protease that can degrade extracellular molecules, provided a suitably acidic environment is present (Briozzo et al., *Cancer Research* 48: 3688–3692 (1988)). Moreover it is abundant in inflamed tissue (S. Bazin and A. Delaunay in *Inflammation, Biochemistry and Drug Interaction*, A. Bertelli and J. C. Houck, Eds., (Excerpta Medica., Amsterdam, 1969), pp 21–28) and known to be important in generating other pharmacologically active polypeptides (L. M. Greenbaum in *Proteases and Biological Control*, E. Reich, D. B. Rifkin and E. Shaw, Eds. (Cold Spring Harbor Laboratory, New York, 1975), pp. 223–228). In terms of its in vivo distribution and function, as well as its specific ability to process LF, cathepsin D is thus uniquely suited to function in the inflammatory response production of this defense polypeptide.

The abundance of the LF catheptic polypeptide in sputum suggests that it may have an important function during pulmonary inflammation or infection. Taken together with the observation that the antimicrobial polypeptide can be generated following cellular processing of epithelium-derived LF, its presence in sputum is also consistent with a potential for it to function in mucosal immunity as well as neutrophil-mediated immunity.

Inhibition of Bacterial Growth by a Polypeptide Corresponding to the First 33 Amino Acids of LF Previous studies indicated that the N-terminal 6 kDa polypeptide fragment of LF functions as a glycosaminoglycan-binding site, and that the glycosaminoglycan (GAG) binding activity of LF was contained within the N-terminal 33 amino acids of the polypeptide. This 33-mer contains two clusters of positively charged (basic) residues, which are thought necessary for the GAG interaction. A 27-mer corresponding to amino acids 7–33 of lactoferrin, which lacked the first cluster of basic residues in LF, but contained the second cluster, only weakly bound GAG. A 27-mer corresponding to amino acids 1–27 of LF which lacked the second cluster of basic residues also exhibited weaker binding to GAG than the 33-mer which contained both basic clusters (Mann et al., *J Biol Chem.* 269: 23661–23667 (1994)).

To investigate whether regions of the molecule involved in GAG binding activity of the 6 kDa LF polypeptide (generated from pepsin digestion) are also involved in the antimicrobial activity of the 6 kDa polypeptide of the present invention, polypeptides of various lengths corresponding to the N-terminal amino acid sequence of LF were tested for the ability to inhibit the growth of *E. coli* 0111. Overnight cultures were grown over a seven hour time course in the presence of 50 $\mu$M of either LF, a 33-mer corresponding to amino acids 1–33 of LF, a 26-mer corresponding to amino acids 7–33 of LF, a 27-mer corresponding to amino acids 1–27 of LF. The 33-mer completely suppressed the growth of these cultures over the length of the entire time course. LF, in contrast, only had a transient growth suppressing effect (FIG. 2). This is consistent with LF and the 33-mer inhibiting bacterial growth via different mechanisms. The growth inhibitory effect of intact LF, but not the 33-mer, can be abolished by saturating the protein with iron, suggesting that LF's primary mode of action is through iron starvation of the bacteria. The difference in the kinetic data for the 33-mer versus LF suggests that the activity of the 33-mer cannot be manifested while it remains within the intact protein. The failure of the 26-mer and the 27-mer to inhibit culture growth emphasizes the importance of retaining both clusters of basic residues, at the termini of the 33-mer, for the antimicrobial functionality of polypeptides derived from the N-terminal LF sequence. These results also indicate that the amino acids responsible for GAG binding in LF previously reported may account for the antimicrobial activity previously observed for the pepsin-derived 6 kDa LF fragment.

Figure 3:
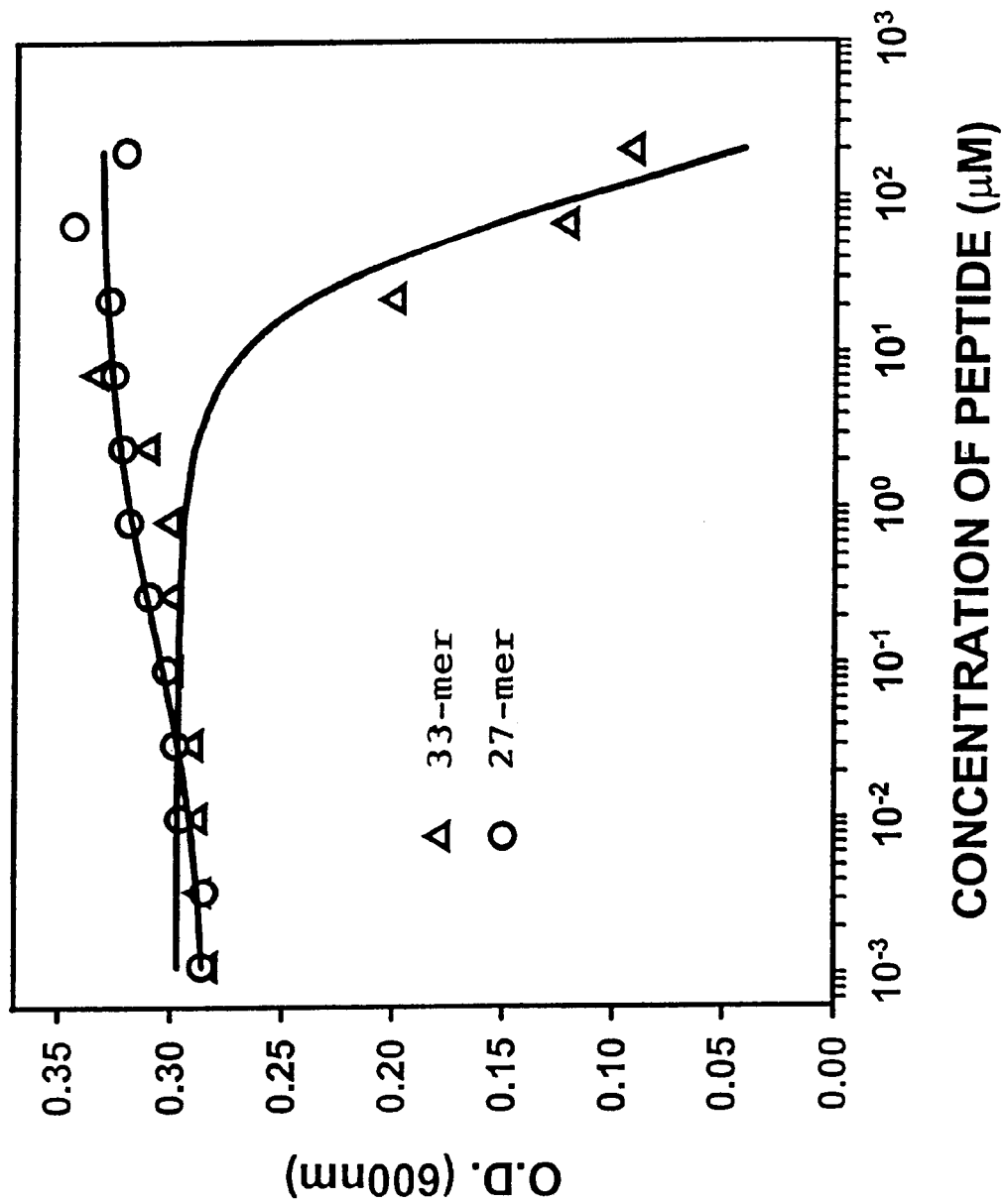
FIG. 3 is a diagrammatic representation of the growth of *E. coli* 0111 at 5 hours in the presence of different concentrations of the 33-mer or 27-mer polypeptides which correspond to amino acid sequences of the N-terminus of LF.

Antimicrobial Dose Response Comparison of Polypeptides with and without Two Basic Clusters To compare the activity of the above described 33-mer which contains both basic clusters, and the above described 27-mer, which contains only one basic cluster, *E. coli* cultures were grown for 5 hours in the presence of varying doses of the two polypeptides. As shown in FIG. 3, the GAG binding 33-mer inhibited bacterial growth with a Minimum Inhibitory Concentration (MIC) of ~2–5 $\mu$M. In contrast, the 27-mer did not inhibit growth (even at concentrations as high as 200 $\mu$M). This data demonstrates that the inhibition of microbial growth by the 33-mer requires an intact first cluster of basic residues and the inhibition is dose-dependent.

Effect of Ionic Strength on the Antimicrobial Activity of the 6 kDa LF Polypeptide It is thought that a first step in the antimicrobial function of many of the naturally occurring cationic host defense polypeptides involves binding of the polypeptide to the surface of the microbe via weak electrostatic interactions with negatively charged sites on the microbial surface. Consistent with this is the observation that many of these host defense polypeptides fail to act against the microbial target under elevated conditions of ionic strength, where the first-step of binding would be inhibited. This type of attenuation of the protective properties of host defense polypeptides can be physiologically relevant to infections that take place in certain tissues where salt accumulation occurs, such as the normal kidney or bladder, or the lung of patients with cystic fibrosis. To define the sensitivity of the antimicrobial activity of a representative of the antimicrobial LF polypeptide fragments to increasing ionic strength.

Figure 4:
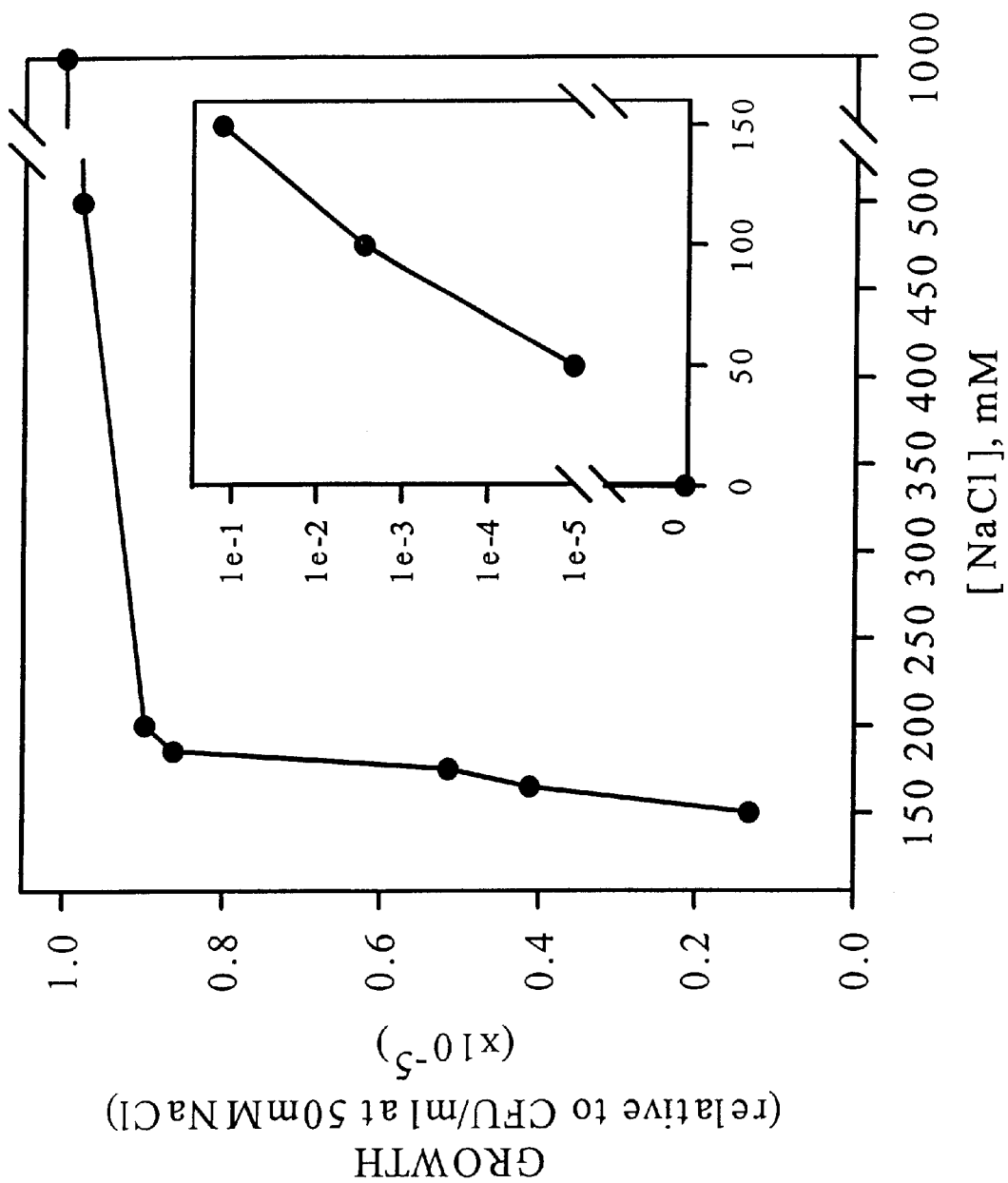
FIG. 4 is a diagrammatic representation of the effect of ionic strength on the antimicrobial activity of the 6 kDa catheptic LF polypeptide fragment.
Figure 5:
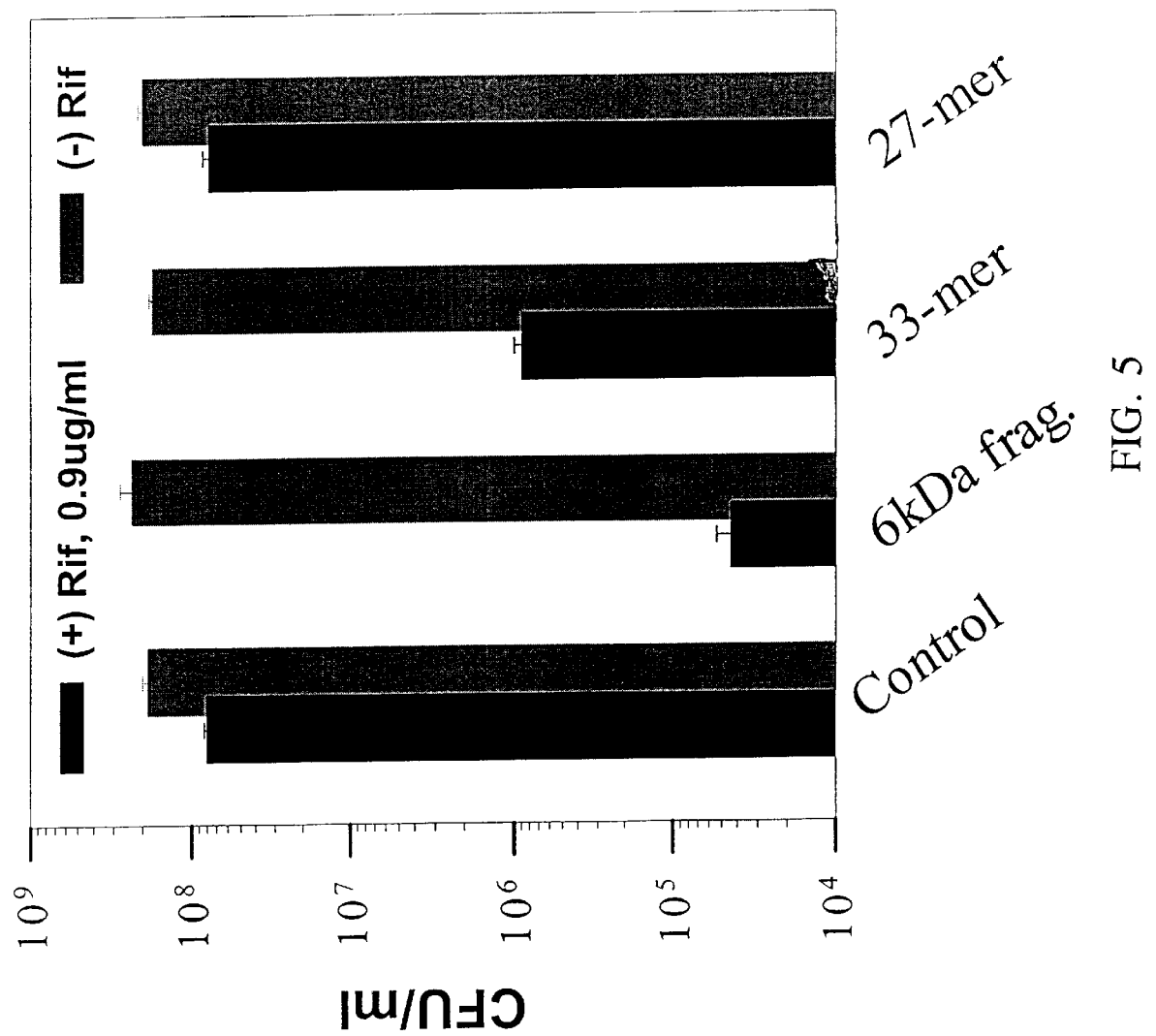
FIG. 5 is a diagrammatic representation of the ability of the polypeptides, 6 kDa LF fragment, 33-mer, and 27-mer to potentiate the antimicrobial activity of rifampicin.

The results of the experiment, presented in FIG. 4, indicate that the growth inhibiting activity of the 6 kDa polypeptide is reduced as ionic strength increases until it is essentially lost as the concentration of NaCl increases to 50 mM above physiological (ionic strengths equal to or greater than 200 mM NaCl). Conversely, at sub-physiological ionic strengths the polypeptide is significantly more potent at inhibiting bacterial growth than it is at physiological salt concentrations. For example, reducing the ionic strength from 150 mM NaCl to 50 mM NaCl reduces the number of viable bacteria after exposure by ~10,000-fold.

These results are significant for several reasons. First, they demonstrate the exquisite sensitivity of the representative antimicrobial polypeptide to subtle perturbations in ionic strength and suggest that the polypeptide inhibits microbial growth via a mechanism that requires an electrostatic interaction with some (yet unknown) microbial target molecule(s), most likely LPS. Second, these results underscore the probability that LF derived host defense polypeptides, and most likely other endogenous host defense polypeptides, of the original (wild-type) sequence will most likely fail to protect patients with cystic fibrosis from pulmonary infections. This is because the lung surface fluid in these patients is reportedly 50–100 mM higher in chloride ion concentration than in the normal lung and, these polypeptides have little or no antimicrobial activity at this ionic strength.

The 6 kDa LF Polypeptide and the 33-mer Increase Bacterial Membrane Permeability The biochemical and structural similarities of the polypeptides of the present invention to other known antibiotic polypeptides, human defensins HNP-1 and HNP-2, bovine tracheal antimicrobial peptide (TAP), porcine protegrins, and others, suggested that this domain in LF may act to inhibit bacterial growth by damaging the permeability characteristics of the bacterial membranes. To test this hypothesis, the ability of the polypeptides of the present invention to increase the potency of rifampicin were tested. Rifampicin is a low molecular weight drug (<1 kDa) that has low membrane permeability but which effectively poisons bacterial cells upon entry into the cytosol.

*E. coli* cultures were exposed to sub-optimal doses of Rifampicin in the presence or absence of sub-optimal doses of the indicated polypeptides (FIG. 5), and were incubated for 6 hours, at which point CFU were determined. The growth inhibiting effects of a sub-optimal dose of rifampicin were dramatically enhanced when administered in combination with a low dose of the antimicrobial polypeptides of the present invention. For example, the addition of a subactive dose (5 $\mu$M) of the 6 kDa polypeptide to cultures exposed to rifampicin reduced the number of viable bacteria resulting after the 6 hr growth period by more than three orders of magnitude. While the negative control 27-mer polypeptide had no significant effect on the antimicrobial activity of rifampicin, the 33-mer, like the 6 kDa polypeptide, potentiated the antibiotic. The synergy between the 33-mer and rifampicin yielded approximately 1% as many viable bacteria as the rifampicin treatment alone. A similar potentiation effect was seen using the antibiotic isoniazid. This indicates that the polypeptides of the present invention function, at least in part by damaging the outer envelope of microbes.

These results also demonstrate the ability of the polypeptides to potentiate the antimicrobial activity of other antimicrobial agents, particularly conventional antibiotics. This indicates that the polypeptides can be used to convert certain types of antibiotic-resistant microbes into the antibiotic-sensitive phenotype. For example, practical concentrations of an otherwise ineffective antibiotic, due to evolved resistance, become efficacious by administration in combination with the polypeptides of the present invention.

Neutralization of Endotoxin in vitro and in vivo by LF Derived Polypeptide

Previous studies have established that the N-terminal 33 residues of human LF represent the minimal sequence that mediates binding of the protein to glycosaminoglycans (Mann et al., *J. Biol. Chem.* 269: 23661–7 (1994)). This sequence contains a cationic head (residues 1–6) and tail (residues 28–33) which combine to form the glycosaminoglycan-binding site. In this study, the endotoxin-neutralizing capacity of a synthetic polypeptide, designated as LF-33, corresponding to the first 33 residues of the secreted form of human LF, was assessed.

Inhibition of Endotoxin-induced *Limulus amebocyte* Lysate Coagulation

The peptide-mediated inhibition of endotoxin-induced *Limulus amebocyte* lysate (LAL) coagulation was measured with a sensitive LAL assay (Zhang et al., *J. Clin. Microbiol.* 32: 416–422 (1994)). Limulus ELISA is an endotoxin assay based on activation of the LAL coagulation by endotoxin and detection of the generated peptide-C immunoreactivity with an ELISA using a monoclonal antibody to the polypeptide. Endotoxin was defined to be neutralized when it lost its ability to activate the LAL enzymes. The 50% endotoxin-neutralizing concentration ($ENC_{50}$) reflects the potency of an anti-endotoxin agent; a low $ENC_{50}$ indicates high potency. Table 2 lists the determined $ENC_{50}$ value of each anti-endotoxin agent against lipid A and four different types of LPS. The potency of each anti-endotoxin agent varied depending on the type of endotoxin. LF-33 was more potent than polymyxin B, on a molar basis, at neutralizing all forms of endotoxin tested. In contrast, LF-27 was approximately 10-fold less potent than LF-33 at neutralizing lipid A and *E. coli* LPS and had no detectable activity against other three LPS. The only difference between the sequence of LF-33 and LF-27 is that LF-27 lacks the first six residues (GRRRRS) at the N-terminus of LF-33. Remarkably, this deletion led to dramatic loss of the endotoxin-neutralizing capacity of the polypeptide in this assay. Binding of serum proteins to endotoxin neutralizes the endotoxin activity in this assay by preventing endotoxin from activating LAL (Emancipator et al., *Infect. Immun.* 60: 596–601 (1992)). Human serum showed varying degrees of the inhibition of endotoxin-induced LAL coagulation, but had no effect on lipid A (Table 2).

TABLE 2

50% endotoxin-neutralizing concentration ($ENC_{50}$) of anti-endotoxin agents determined with Limulus ELISA

| | $ENC_{50}$ (mean +/− SD, $\mu$M or percent concentration) against endotoxin (200 EU/ml) | | | | |
|---|---|---|---|---|---|
| Agents | Lipid A | *E. coli* LPS | *S. abortus* LPS | *P. aer.* LPS | *N. min.* LPS |
| LF-33 | 0.10 +/− 0.017 | 0.52 +/− 0.078 | 0.39 +/− 0.054 | 2.08 +/− 0.37 | 3.08 +/− 0.44 |
| LF-27 | 0.63 +/− 0.093 | 7.45 +/− 1.12 | >300 | >300 | >300 |
| Polymyxin B | 0.19 +/− 0.021 | 1.95 +/− 0.26 | 18.2 +/− 2.85 | 3.91 +/− 0.73 | >100 |
| Human serum | >50% | 0.03% +/− 0.005% | 2.1% +/− 0.29% | 0.63% +/− 0.11% | 2.52% +/− 0.41% |

LF Polypeptides Neutralize Endotoxin Activity from Lipid A Portion of LPS

Figure 6:
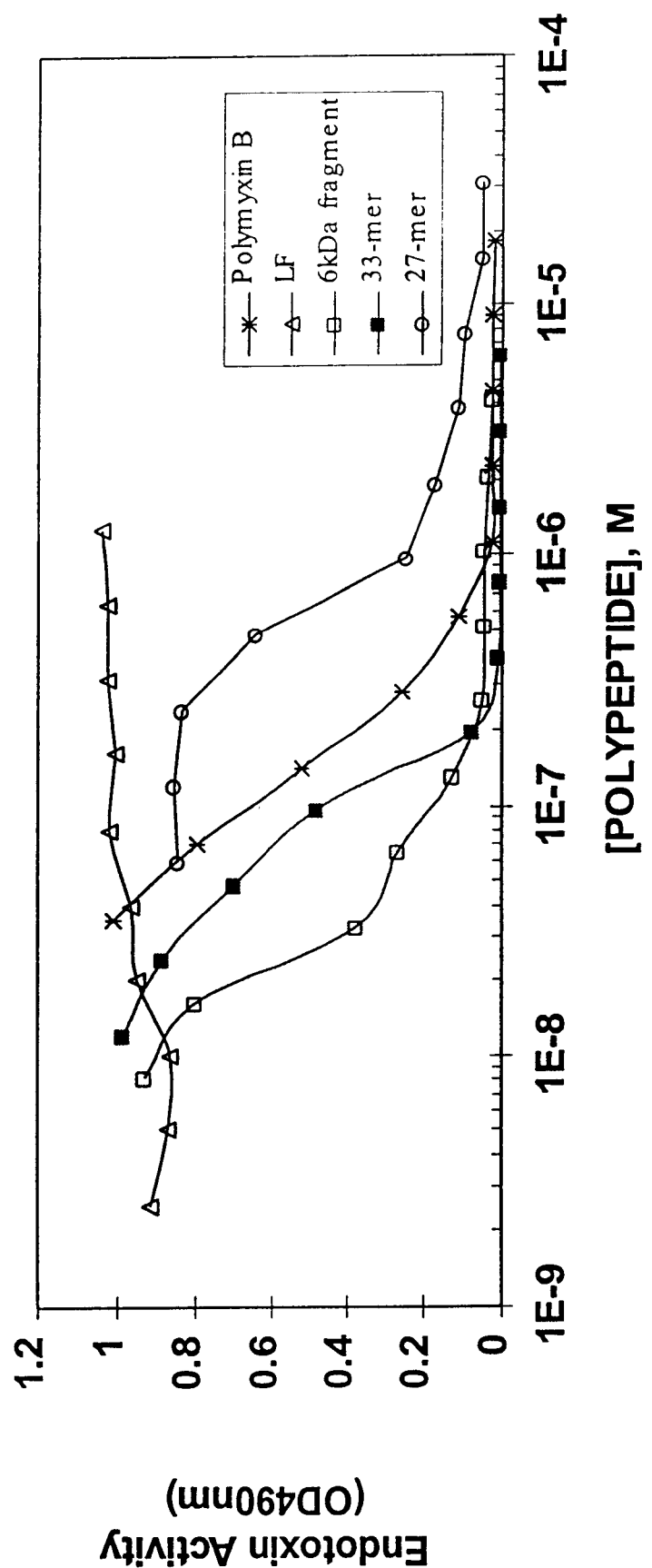
FIG. 6 is a diagrammatic representation of the ability of the indicated concentrations of the 6 kDa host-defense polypeptide, 33-mer, 27-mer, LF, and polymyxin B to neutralize the endotoxin activity of isolated lipid A.

The lipid A region of the LPS molecule is primarily responsible for the inflammatory and toxic effects of LPS. When LPS is released from the microbe, the lipid A portion may become more accessible. The following assays were performed to determine the potential of various amino-terminal LF polypeptides to neutralize the endotoxic activity of the lipid A portion of LPS. LF, the 6 kDa fragment of LF, LF-33, LF-27, and polymyxin B were each tested for the ability to neutralize the endotoxin activity of lipid A from *E. coli* 0113 (30 ng/ml), using a LAL assay. The results of this experiment are presented in FIG. 6. Although LF demonstrated no appreciable lipid A neutralizing activity, the 6 kDa LF fragment, LF-33 and LF-27 neutralized lipid A with similar but non-identical potencies, each of which were comparable to that of polymyxin B, the standard in the industry. This indicates that LF-27, which has only one cluster of basic amino acids, is as potent in neutralizing a form of endotoxin that lacks the large, bulk, oligosaccharide portion of LPS as the polypeptides which contain two clusters of basic amino acids. This observed ability of the 27-mer to neutralize the more readily accessible lipid A tail indicates that the clusters of positively charged residues at the termini of the 33-mer bind to the anionic sites in the oligosaccharide portion of LPS, or the head group of lipid A, but that the hydrophobic intervening sequence spanning the two clusters is critically important for binding to the lipid A region and neutralizing its inflammatory activities. The endotoxin activity of the smaller fragments of LF indicate that endotoxin-neutralizing activity of these small polypeptides is masked when in the context of the intact LF molecule.

Suppression of Endotoxin Induced TNF-α Secretion by LF-33

Figure 7:
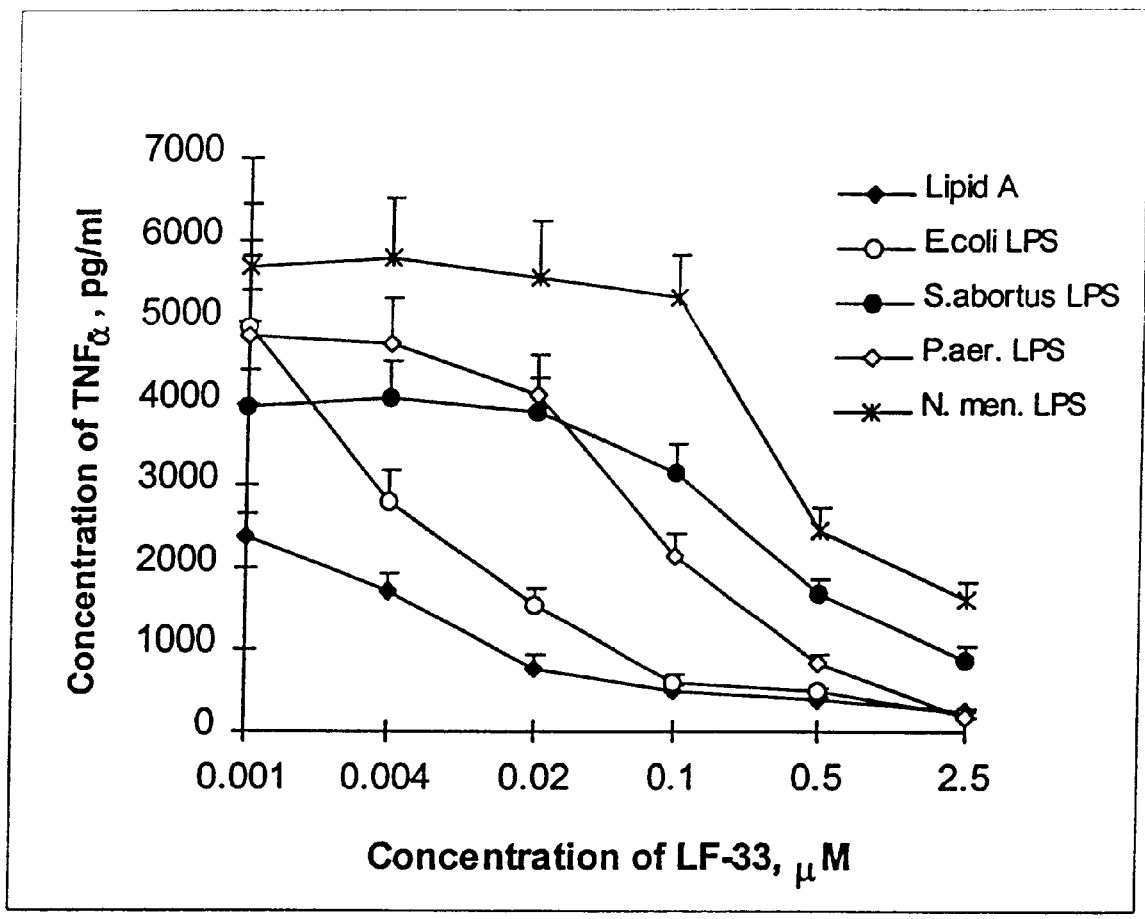
FIG. 7 is a diagrammatic representation of the dose-dependent suppression by LF-33 (the 33-mer) of endotoxin-induced TNF-α secretion by the mononuclear leukocytic cell line RAW 264.7. Endotoxin at 10 ng/ml was incubated at 37° C. for 1 h with LF-33 at concentrations indicated before being exposed to RAW 264.7 cells. Data are the means of triplicates in representative experiments.

Suppression of endotoxin-induced TNF-α secretion by a macrophage cell line RAW 264.7 was also measured (Kelly et al., *Infect. Immun.* 59: 4491–6 (1991)). RAW 264.7 cells secret TNF-α upon exposure to endotoxin (M. R. Ruff and G. E. Gifford, *Lymphokines* 2: 235–272 (1981)). A linear relationship between TNF-α secretion and endotoxin concentration was observed at endotoxin concentrations below 20 ng/ml for the lipid A and various LPS used in this study, and a concentration of 10 ng/ml of endotoxin was selected for the TNF-α-inducing experiments. Mixing endotoxin with increasing concentrations of LF-33 resulted in a dose-dependent suppression of endotoxin-induced TNF-α secretion (FIG. 7). Similar to the results of the LAL assay, the potency of LF-33 varied depending on the type of endotoxin. The LF-33 concentration needed to suppress 50% TNF-α secretion induced by endotoxin (10 ng/ml) was approximately 0.01 µM for *E. coli* LPS and lipid A, 0.1 µM for LPS from *P. aeruginosa*, and 0.5 µM for LPS from *S. abortus equi* and *N. meningitidis*. The effects of LF-27, polymyxin B, and human serum on endotoxin-induced TNF-α secretion are shown in Table 3 for a comparison. LF-33 exhibited a slightly higher potency than polymyxin B in suppressing TNF-α secretion induced by different types of endotoxin, whereas an equal molar concentration of LF-27 or 10% human serum had no effect on endotoxin-induced TNF-α secretion.

TABLE 3

Suppression by anti-endotoxin agents of endotoxin-induced TNF-α secretion by RAW264.7 cells+

| | TNF-α secretion (mean +/– SD, pg/ml) induced by endotoxin (10 ng/ml) | | | | |
|---|---|---|---|---|---|
| Agents | Lipid A | *E. coli* LPS | *S. abortus* LPS | *P. aer.* LPS | *N. min.* LPS |
| endotoxin control | 2,386 +/– 269 | 4,928 +/– 896 | 3,969 +/– 443 | 4,813 +/– 571 | 5,658 +/– 770 |
| LF-33 (2.5 µM) | 239* +/– 29.6 | 211* +/– 31.4 | 886* +/– 149 | 164* +/– 23.3 | 1,624* +/– 203 |
| LF-27 (3 µM) | 3,182 +/– 412 | 4,912 +/– 588 | 3,985 +/– 497 | 4,633 +/– 603 | 7,306 +/– 1008 |
| Polymyxin B (2.5 µM) | 537* +/– 77.9 | 314* +/– 42.6 | 1,115* +/– 181 | 246* +/– 32.5 | 2,829* +/– 455 |
| Human serum (10%) | 2,663 +/– 337 | 4,817 +/– 964 | 5,726 +/– 1126 | 4,428 +/– 677 | 8,817 +/– 1711 |

*One-tailed P value <0.05 compared with the LPS controls in the unpaired t-test.
+endotoxin was incubated with test agents at indicated concentrations in the table at 37° C. for 1 h before being exposed to RAW 264.7 cells.

Figure 8:
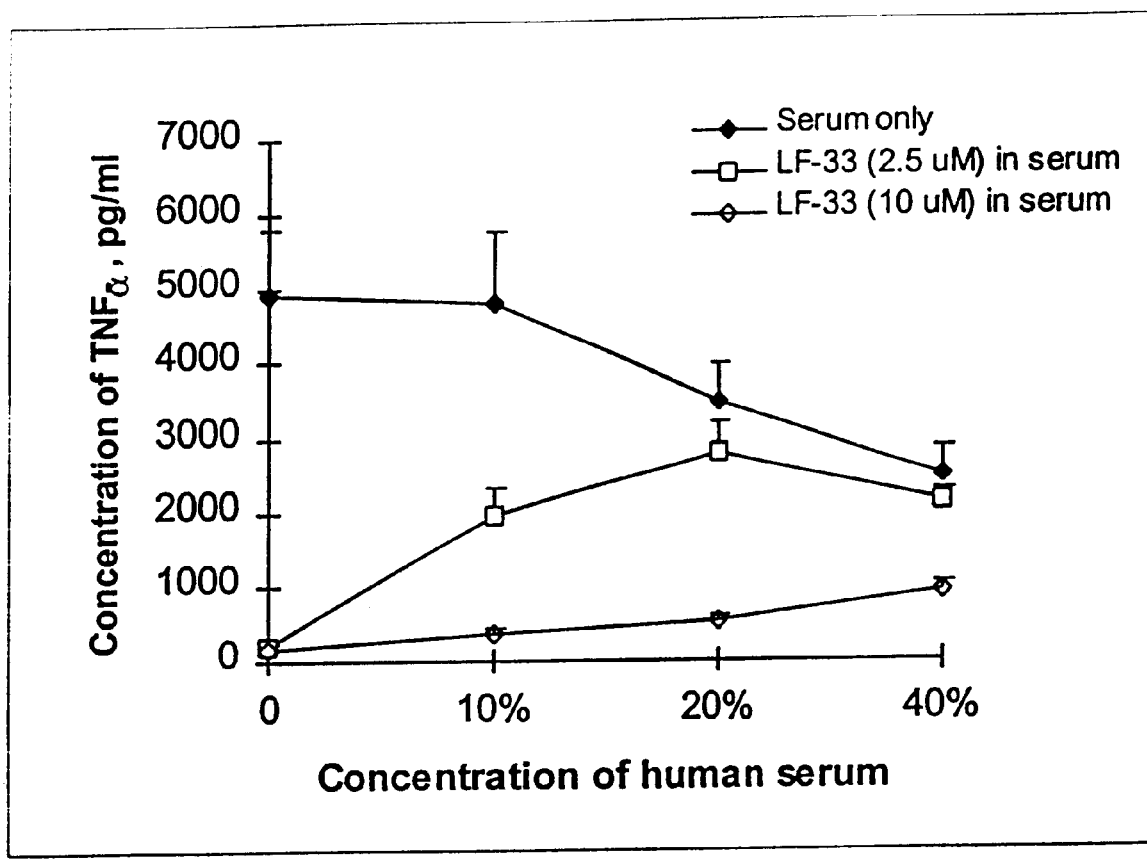
FIG. 8 is a diagrammatic representation of the dose-dependent suppression by LF-33 of endotoxin-induced TNF-α secretion by RAW 264.7 cells in the presence of human serum. *E. coli* LPS at 10 ng/ml was incubated at 37° C. for 1 h with human serum and LF-33 at concentrations indicated before being exposed to RAW 264.7 cells. Data are the means of triplicates in representative experiments.

Effect of Human Serum on the LF-33 Suppression of Endotoxin-induced TNF-α Secretion To test the suppression of endotoxin-induced TNF-α secretion under more physiological conditions, LF-33 or polymyxin B was added to human serum (final concentration 10%) before the addition of endotoxin. As shown in Table 4, the suppressive effect of the polypeptides was attenuated substantially in the presence of 10% human serum, although the serum effect could be overcome by increasing the concentration of LF-33 (Table 4 and FIG. 8). However, if the polypeptide was mixed with endotoxin 5 min before the addition of serum, the effect of the serum on the neutralization of endotoxin by the polypeptides was greatly reduced (Table 5).

TABLE 4

Suppression by anti-endotoxin polypeptides of endotoxin-induced TNF-α secretion by RAW264.7 cells in culture medium containing -10% human serum

| Polypeptides | TNF-α secretion (mean +/− SD, pg/ml) induced by endotoxin (10 ng/ml) | | | | |
|---|---|---|---|---|---|
| | Lipid A | E. coli LPS | S. abortus LPS | P. aer. LPS | N. min. LPS |
| endotoxin control | 2,663 +/− 337 | 4,817 +/− 964 | 5,726 +/− 1126 | 4,428 +/− 677 | 8,817 +/− 1711 |
| Polymyxin B (2.5 μM) | 1,209* +/− 199 | 1,259* +/− 321 | 4,090 +/− 806 | 4,206 +/− 956 | 8,181 +/− 1,032 |
| LF-33 (2.5 μM) | 1,518* +/− 311 | 1,938* +/− 376 | 5,627 +/− 1037 | 2,776* +/− 478 | 7,998 +/− 976 |
| LF-33 (10 μM) | 185* +/− 25.6 | 369* +/− 67.1 | 1,191* +/− 264 | 833* +/− 138 | 6,473 +/− 787 |

*One-tailed P value <0.05 compared with the control in the unpaired t-test.
+endotoxin was incubated at 37° C. for 1 h with polypeptides at concentrations indicated in the table in culture medium containing 10% human serum before being exposed to RAW 264.7 cells.

TABLE 5

Suppression by anti-endotoxin polypeptides of endotoxin-induced TNF-α secretion by RAW264.7 cells in culture medium containing 10% human serum: effect of the mixing sequence with serum

| | TNF-α secretion (mean +/− SD, pg/ml) induced by endotoxin (10 ng/ml) | | | |
|---|---|---|---|---|
| | E. coli LPS mixing with | | P. aer. LPS mixing with | |
| Polypeptides | polypeptide first | serum first | polypeptide first | serum first |
| LPS control | 4,817 +/− 964 | | 4,428 +/− 677 | |
| LF-33 (2.5 μM) | 575** +/− 115 | 1,938* +/− 376 | 610** +/− 160 | 2,776* +/− 478 |
| Polymyxin B (2.5 μM) | 525** +/− 130 | 1,259* +/− 321 | 883** +/− 261 | 4,206 +/− 956 |

*One-tailed P value <0.05 compared with the control in the unpaired t-test.
**One-tailed P value <0.01 compared with the group labeled as 'serum first' in the unpaired t-test.

Effect of LF-33 on Endotoxin-induced Lethality and Serum TNF-α Level in the Galactosamine-sensitized Mouse Model Mice are typically resistant to endotoxin. However, the sensitivity of mice to endotoxin can be enhanced more than 1000-fold by co-injection with a liver specific inhibitor galactosamine (Freudenberg M. A., and C. Galanos, *Infect. Immun.* 59: 2110–2115 (1991); Galanos et al., *Proc. Natl. Acad. Sci. USA* 76: 5939–5943 (1979)). An essential feature of this in vivo model is that systemically released TNF-α causes liver damage due to TNF-α-mediated liver cell death, which can be scored by measuring lethality. Intraperitoneal injection of 125 ng E. coli LPS per animal induced nearly 100% lethality in the galactosamine-sensitized mice. As shown in Table 6, the endotoxin-induced lethality was dramatically reduced by injecting LF-33. Small amounts of LF-33 (2.5 μg per animal), when injected simultaneously with endotoxin, reduced the lethality from 93% (14 deaths out of 15) to 6% (1 death out of 15). In addition, LF-33 also significantly reduced the lethality when injected intravenously (i.v.) 10 min subsequent to the intraperitoneal (i.p.) injection of endotoxin (Table 6), albeit 40-fold greater amount of LF-33 were required. The protection was correlated with the reduction of the mouse serum TNF-α level (Table 6).

TABLE 6

Protection of animals from the lethality of LPS by LF-33 in the galactosamine-sensitized mouse model

| Dose of i.p. injection per mouse* | Lethality (dead/total) | Serum TNF-α level (mean +/− SD, pg/ml) |
|---|---|---|
| (1) LPS 5 ng | 1/5 | Not Done |
| (2) LPS 25 ng | 3/5 | Not Done |
| (3) LPS 125 ng | 14/15 | 5,801 +/− 3,120 |
| (4) LPS 125 ng mixed with 2.5 μg LF-33 | 1/15** | 885*** +/− 657 |
| (5) LPS 125 ng + 20 μg LF-33 (i.v.) | 5/5 | 4,611 +/− 1,897 |
| (6) LPS 125 ng + 100 μg LF-33 (i.v.) | 3/15** | 1,125*** +/− 1,166 |

*In Group (1) to (4), all materials were injected i.p, whereas in Group (5) and (6), LPS and galactosamine (15 mg per mouse) were injected i.p., but LF-33 was injected i.v. 10 min after LPS injection. The strain of mice was NIH/Swiss, weighing between 20 and 22 grams per mouse. The total volume for i.p. and i.v. injection per mouse was 0.5 ml and 0.2 ml respectively.
**One-tailed P value <0.01 compared with Group (3) in the Fisher's exact test.
***One-tailed P value <0.01 compared with Group (3) in the unpaired t-test.

Figure 9:
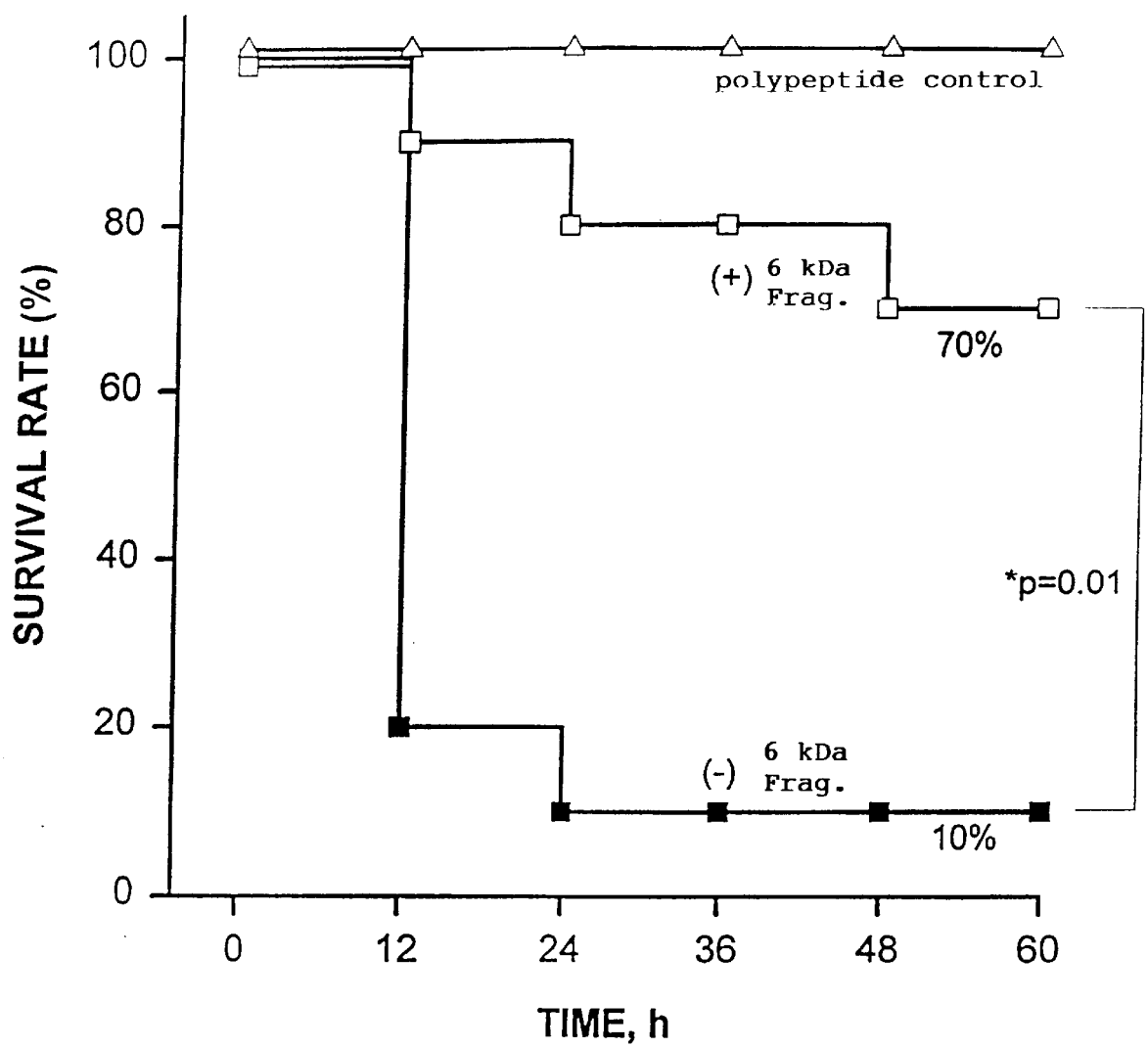
FIG. 9 is a diagrammatic representation of the in vivo protective potential of the 6 kDa LF fragment in host-defense against bacterial infection.

Effect of LF 6 kDa Catheptic Fragment on Bacteremic Lethality in the Galactosamine-sensitized, Leukopenic Mouse Model The ultimate protective potential of the LF 6 kDa polypeptide in a host-defense against bacterial infection was determined by testing in an acute, galactosamine-sensitized, leukopenic mouse model system (Bucklin et al., *J. Infect. Dis.* 174: 1249–1254 (1996)). In this model, mice were made leukopenic to suppress their endogenous host defense systems and then sensitized to the effects of Gram-negative endotoxins by galactosamine treatment while injecting a lethal intraperitoneal dose of *E. coli*. The data, represented in FIG. 9, shows that simultaneous injection with the 6 kDa catheptic fragment of human LF (100 μM, i.p.) dramatically increased the survival rate of infected animals, from 10% in untreated animals to 70% in polypeptide treated animals (one tailed P value <0.01 using Fisher's Exact Test). This rescue from lethality dramatically illustrates the protective potential of the polypeptide in vivo and is likely due to its combined antimicrobial and anti-endotoxin properties. This result indicates that the polypeptide has significant utility as a therapeutic agent.

Anti-mycobacterial Activity of the Antimicrobial Polypeptides

Figure 10:
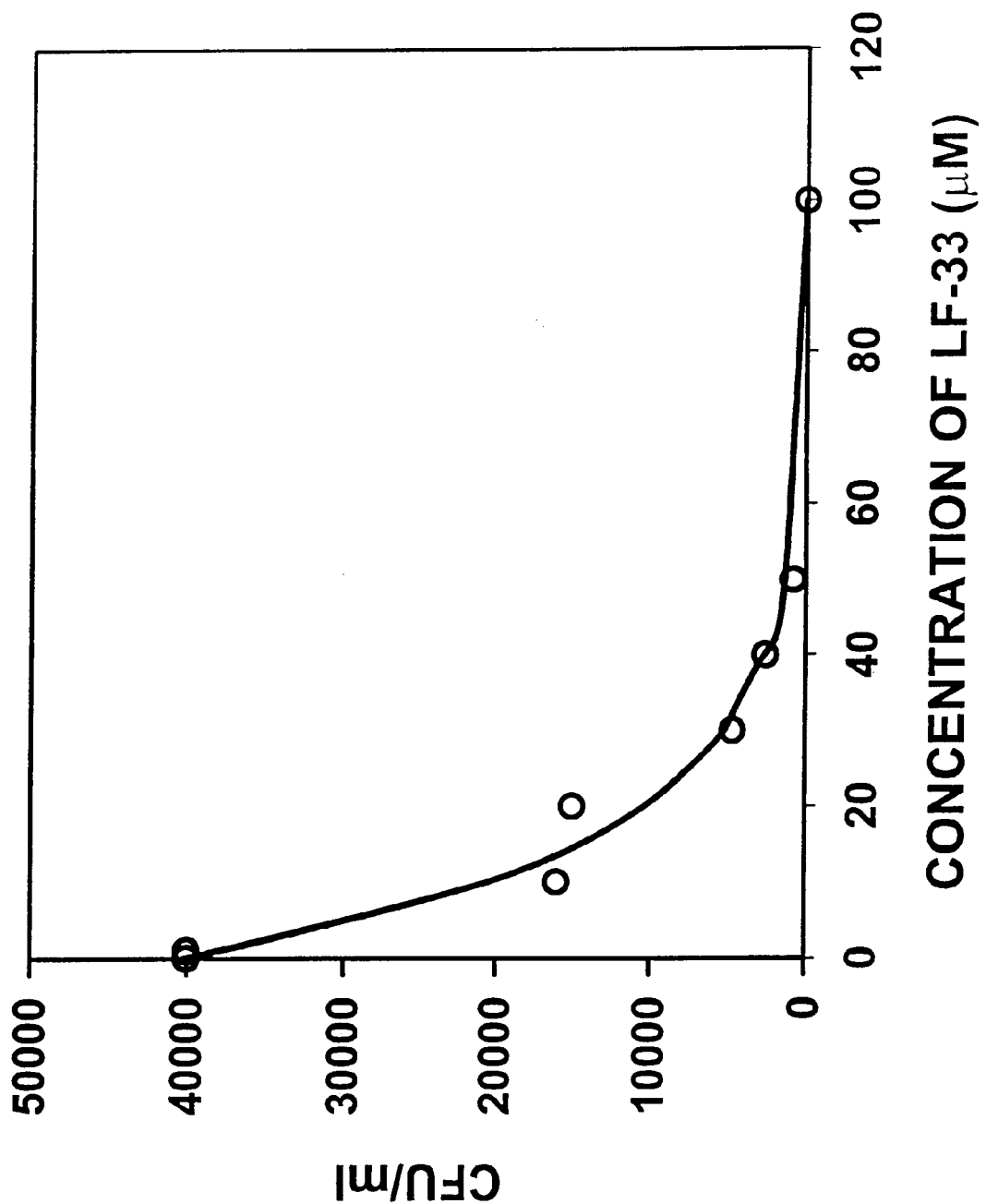
FIG. 10 is a diagrammatic representation of the antimicrobial effects of various concentrations of LF-33 (33-mer) on the growth of Mycobacteria, *M. smegmatis* BH1.

Bacteria of the genus Mycobacteria include *M. tuberculosis, M. smegmatis, M. leprae, M. bovis,* and others. These microbes are responsible for two of the most dreaded diseases in human history; tuberculosis and leprosy. Mycobacteria have an unusually thick cell wall with a complex chemical composition rich in lipid content, which confers unique properties to these microbes, especially a significant resistance to many types of antibiotics. Experiments were performed to determine whether the LF derived polypeptides could inhibit the growth of Mycobacteria. Equal density cultures of *M. smegmatis* were grown in the presence or absence of LF-33 (50 μM final concentration), for 16 hours and the resulting viable cells were determined. The results, presented in Table 7, indicated an average of 94% killing by the presence of LF-33. In a complementary experiment, cultures of *M. smegmatis* were grown in the presence of either 10, 20, 30, 40, 50, or 100 μM LF-33, after which the resulting viable cells were determined. The results, presented in FIG. 10, indicate a dose dependent inhibition of mycobacterial growth by the LF-33 polypeptide. The 33-mer shows an anti-mycobacterial MIC value of not more than 10 μM and gives approximately 94% killing at a concentration of 50 μM.

These experiments demonstrate that a representative member of the antimicrobial LF polypeptides, the 33-mer, inhibits the growth of Mycobacteria. Although these experiments were performed with the faster growing *M. smegmatis* BH1 species, similar results have also been produced with the H37Ra strain of *M. tuberculosis*. The unpredictable inhibition of Mycobacteria by LF-33 is surprising given the unusual waxy, low permeability, properties of the cell membrane of these microbes.

TABLE 7

Anti-mycobacterial activity of LF-33

| Experiment | Untreated CFU/ml | 50 μM LF-33 CFU/ml (% killed) |
|---|---|---|
| 1 | 40,000 | 780 (98%) |
| 2 | 31,500 | 3,000 (90%) |
| 3 | 21,000 | 1,000 (95%) |
| Average | | (94%) |

Methods of the Invention

Immuno-reagents. Antibodies against the N-terminus of human LF were raised in rabbits immunized with a multiple antigenic polypeptide form (J. Tam, Proc. *Natl. Acad. Sci. USA* 85: 5409–5413 (1988)) of the first seventeen residues of the mature form of human LF. This sequence contains the first of two clusters of basic amino acids that are simultaneously required for the binding of LF to anionic polysaccharides like heparin (Mann et al., *J. Biol. Chem.* 269: 23661–7 (1994)). These antibodies immunoblot intact LF and fragments that contain its N-terminus but do not cross-react with any other polypeptides tested, including human transferrin or proteolytic fragments derived from it. The antibodies were used for immunoblotting as an antiserum diluted 1:3,000 in buffered saline containing 1% albumin as a carrier and membrane-blocking agent. Secondary antibody was an alkaline-phosphatase conjugated goat anti-rabbit IgG from Kirkegaard & Perry Laboratories, and the BCIP/NBT detection system was used (E. Harlow and D. Lane, Eds. *Antibodies: A Laboratory Manual* (Cold Spring Harbor Laboratory, Cold Spring Harbor, N.Y. (1988)), chap. 12).

Immunoblotting. Standard procedures were followed for gel electrophoresis and immunoblotting (E. Harlow and D. Lane, Eds. *Antibodies: A Laboratory Manual* (Cold Spring Harbor Laboratory, Cold Spring Harbor, N.Y. (1988)).

Sample preparation. Outdated frozen human colostrum was obtained from a local mother's milk bank. All other body fluid samples were obtained from the Tissue Procurement Center at the University of Virginia Health Sciences Center or from volunteer donors in the laboratory. Dermal exudates ("pus") from furuncles, gingival plaque scrapings, saliva and sputum expectorate samples were collected into sterile microfuge tubes and brought to 1× with SDS-PAGE sample buffer containing 1 μg/ml leupeptin, aprotinin, and pepstatin A to inhibit proteases. Sample buffer contained 0.1% SDS and, +/-5% β-mercaptoethanol as a reducing agent. These were immediately boiled and stored at –80° C. until separated on 5–20% linear gradient polyacrylamide gels. The volume of original tissue fluid loaded per gel lane measured between 5–20 ml, depending on the sample. Separated polypeptides were electrophoretically transferred to nitrocellulose membranes (Millipore Corp.) in a transfer buffer that was empirically determined to permit optimal transfer of small cationic polypeptides. Electrophoretic transfer occurred for 2 h at a constant 150 volts in 30% methanol containing 0.01% SDS, 25 mM TRIS base and 192 mM glycine, in a Hoeffer TE-22 mini-transfer apparatus. Ponceau S was used to reversibly stain total proteins transferred to the membrane prior to photographing and immunostaining. Scanning densitometry of the immunostained bands was performed using a Hewlet Packard ScanJet IIcx/T laser scanner and the Image densitometry analysis program from the N.I.H.).

Cell isolation. Primary cultures of phagocytes were isolated from peripheral human blood initially by the Ficoll (Organon Teknika Corp.) density gradient method (J. E. Coligan, A. M. Kruisbeek, D. H. Margulies, E. M. Shevach and W. Strober, Eds. *Current Protocols in Immunology* (John Wiley & Sons, New York, N.Y. 1991), chap. 7). Contaminating red blood cells were removed from the neutrophil fraction by differential sedimentation in dextran T-500, 0.9% saline, followed by hypotonic lysis. Monocytes were further isolated from lymphocytes by countercurrent centrifugal elutriation in a Beckman J2-21M centrifugal elutriator (Beckman Instruments) as described (ibid). All cell experiments were initiated within 30 min of isolating the fresh phagocytes. For the phagocyte coculture experiments, monocytes and neutrophils isolated from the same unit of blood were recombined and the pooled mixture split into two halves, one of which was immediately lysed as a pre-activated control in lysis buffer; TRIS buffered saline containing 1% Triton X-100 and a cocktail of protease inhibitors. The remaining cells were cocultured for 5 h at 37° C. in serum-free RPMI medium (Life Sciences, Gaithersburg, Md.) following activation with 2 mM fMet-Leu-Phe (Sigma Chemicals). The activated cocultures were then lysed in lysis buffer and the detergent lysate combined with the overlying culture medium in preparation for heparin purification of LF fragments. Heparin-binding polypeptides in the activated and pre-activated coculture lysates were isolated in batch mode by heparin-chromatography following clarification of the lysates by centrifugation. Polypeptides eluted from the heparin-Sepharose by 750 mM NaCl were then electrophoresed under reducing conditions and immunoblotted as described above. For the experiments in which neutrophils and monocytes were studied separately, each culture was incubated for 3 h following activation and the monocyte cultures were supplemented with 50 mg of purified human milk LF since they had no endogenous LF. The culture medium was then removed prior to lysing the cells with the 1% Triton X-100 containing buffer described above and heparin-binding molecules were isolated from the culture media and cell extracts separately.

Purification of LF from human colostrum and proteolytic liberation of the antimicrobial domain in vitro. Frozen colostrum was thawed at 37° C. and defatted by centrifugation for 40 min at 10,000×g at 4° C. The underlying skim milk was defatted a second time and then converted to whey by incubation for 40 min at 40° C. following acidification with HCl to pH 4.7. The coagulum was removed by centrifugation at 4° C. for 40 min at 10,000×g and the supernatant whey diluted with 4 volumes of TRIS buffered saline, pH 7.4, prior to fractionation by ion exchange chromatography to isolate LF. After binding the LF in the diluted whey to CM-Sepharose Fast Flow (Pharmacia), the column was washed exhaustively with phosphate buffered saline and the bound proteins are eluted with a gradient of ionic strength from 0.15–1.0 M NaCl in the same wash buffer. LF typically elutes as a single peak at approximately 550 mM NaCl that was homogeneous by SDS-PAGE analysis and N-terminal amino acid sequencing. The LF peak was concentrated 4-fold by Speed Vac centrifugation and then dialyzed exhaustively at 4° C. against 50 mM NaCl using 30,000 MWCO tubing (Spectrum). Prior to digestion with bovine spleen cathepsin D (Sigma), the dialyzed LF was brought to 150 mM NaCl and 50 mM sodium acetate, pH 3.5, and then digested to completion for 36 h at 37° C. with a 1:200 (w:w) ratio of cathepsin D to LF. LF concentration was determined spectrophotometrically at 280 nm (using E280nm 1 cm 0.1%=1.0402). For the time course digestion experiments, samples equivalent to 20 mg of the original LF were removed at the various indicated times, treated with 1 mg/ml pepsatin A and boiled in SDS-PAGE sample buffer to terminate proteolysis and stored frozen until electrophoresing at the end of the time-course. To prepare the antimicrobial fragment in bulk, the 36 h LF digest was then passed over a pepstatin A-agarose column (Sigma) to remove any active cathepsin D (L. B. Larsen and T. E. Petersen in Aspartic Proteinases: Structure, Function, Biology, and Biomedical Implications, K. Takaahashi, Ed., (Plenum Press, New York, 1995) pp. 279–283) and the flow-through fraction treated with 1 mg/ml pepstatin A to inhibit any residual cathepsin D activity. The flow-through was then diluted to physiological pH and ionic strength with sodium bicarbonate, NaOH, and NaCl in preparation for heparin-purification and brought to 1 mM with ferrous chloride to saturate with iron any trace levels of undigested LF that might be present (but undetectable by SDS-PAGE or immunoblotting). The antimicrobial polypeptide was then bound to heparin-Sepharose (Pharmacia) and eluted with a gradient from 150 mM to 1 M NaCl following an extensive column wash with phosphate buffered saline. The purified polypeptide was dialyzed against distilled water prior to drying to completion and storage at −80° C. Generation of the corresponding fragment by pepsinolysis was essentially as per the cathepsin digest except that the digest was performed for 4 h at 37° C. in 50 mM glycine, pH 3.0, with a 3:100 (w:w) ratio of pepsin:LF.

LF digestion with cathepsin D and heparin. LF (10 μg) was digested with cathepsin D at pH 5, as described above, for the indicated times, in either the absence or presence of a ten fold molar excess of heparin (porcine mucosa heparin, MW ~7–15 kDa, from Sigma Fine Chemicals).

Mass spectrometry. MALDI mass spectrometry (W. T. Moore, *Methods Enzymol* 289: 520–42 (1997)) was performed on the heparin-purified 6 kDa catheptic fragment by the Protein and Carbohydrate Structure Facility of the University of Michigan Medical School, Ann Arbor, Mich., or by the American Red Cross.

Antimicrobial assay for LF polypeptides. Cultures of *E. coli* 0111 (American Type Culture Collection #43887) were grown at 37° C. in 1% bactopeptone (BP) (Difco) in Dulbecco's phosphate buffered saline (dPBS) (Mediatech) with aeration by shaking (225 rpm). overnight cultures were diluted 8,000-fold in 2×concentrated BP/dPBS and mixed with an equal volume of sterile endotoxin-free distilled water containing serial dilutions of the polypeptide to be tested. The final assay volume was 300 mL in a 12 mm×75 mm polypropylene tube (Falcon) with an ultimate dilution of the overnight cultures of 1:16,000 to yield an original inoculum of ~1–2×$10^4$ CFU/ml. The final assay medium was physiological in ionic strength, 1% bactopeptone in 1×Dulbecco's phosphate buffered saline. Cultures were grown for 6 h at 37° C. with aeration as above and then cell density determined by measuring CFU/ml for each assay culture tube. Serial dilutions of each assay tube were plated on Luria Broth bactoagar and incubated for 24 h at 37° C. prior to counting colonies. All assays were done in triplicate and the standard deviation calculated for each concentration of inhibitor. Culture density at the beginning and end of the 6 h growth period was also determined from triplicate cultures lacking any polypeptide inhibitors. Untreated cultures typically grew to 1–2×$10^8$ CFU/ml in 6 h under these assay conditions.

Time course of *E. coli* growth in the presence of LF polypeptides. *E. coli* cells, clinical isolate strain 0111, were obtained from ATCC. Cultures were routinely grown overnight at 37° C. with aeration by shaking at 220 rpm in 1% BP/PBS (1% Bactopeptone (from Difco Laboratories, Detroit, Mich.) prepared to physiological ionic strength in phosphate buffered saline, "PBS" (Mediatech Inc., Herndon, Va.)), at pH 7.4. Overnight cultures were diluted 1:20 into 1% BP/PBS containing the indicated polypeptides at 50 μM and incubated for the indicated times. Culture growth was monitored spectrophotometrically by measuring optical density at 600 nm at each indicated time point.

Dose response of *E. coli* 0111 cells in the presence of LF polypeptides. *E. coli* were cultured as described above, for 5 hr in the presence of varying concentrations of polypeptide 33-mer or the related 27-mer. Inhibition of culture growth was determined spectrophotometrically as described earlier.

Potentiation of Rifampicin by LF polypeptides. *E. coli* 0111 were grown overnight as described above. Overnight cultures were then diluted 1:16,000 in 1% BP/PBS containing 0.9 µg/ml Rifampicin (Sigma-Aldrich Fine chemicals) and 5 µM LF polypeptides as indicated. Control cultures were those not exposed to any polypeptide. The diluted cultures were then incubated at 37° C. for 6 hr with aeration by shaking. The number of viable bacteria were then determined by dilution plating samples from each group and subsequently counting colony forming units (CFU). All values represent the average of duplicate independent experiments.

Anti-mycobacterial analysis of LF-33. Mycobacterial cultures, *M. smegmatis* BH1, were initially grown to log phase in 7H9 broth (American Type Culture Collection Culture Medium 1507, Supplemented Middlebrook 7H9 Broth) before determining culture density by spectrophotometric means (optical density at 600 nm, where O.D. $0.23=10^8$ cells). Cultures were then diluted to $2 \times 10^4$ CFU/ml with 7H9 broth and 570 µl of diluted cells (~$10^4$ CFU) were then mixed with 30 µl of a concentrated stock solution of the LF-33 polypeptide such that the final concentration of the polypeptide in the culture medium was as indicated (50 µM for Table 7, and variable for FIG. 10). Cultures were then incubated for 16 hours at 37° C. after which time 50 µl was removed and plated in serial dilutions on 7H9 agarose plates to determine number of viable cells by the conventional colony plating method.

Determining ionic strength effect on antimicrobial activity. *E. coli* were cultured overnight as described earlier. Overnight cultures were then diluted 1:16,000 into 1% BP that was buffered with 4 mM sodium bicarbonate and supplemented with varying concentrations of sodium chloride from 50 µM to 1 M. Polypeptide-treated cultures also received 25 µM 6 kDa LF polypeptide whereas control cultures at each salt concentration received no polypeptide. After 6 hr of growth at 37° C. with aeration, the number of viable bacteria was determined by dilution plating samples from each group and subsequently counting CFU. To control for the effects of salt alone on culture growth, the ratio of CFU in polypeptide treated cultures to that in untreated control cultures, grown in the same salt concentration but lacking any polypeptide treatment, was calculated for each salt concentration examined. These values were then normalized to the ratio calculated for CFUs measured at 50 µM, the lowest salt concentration tested, and plotted on the Y-axis versus increasing concentration of salt on the X-axis. Thus, the Y-axis shows the growth inhibitory effect of the 6 kDa polypeptide at each of the concentrations of NaCl tested, relative to its antimicrobial activity at 50 µM NaCl. The inset shows a semi-log plot of the results for sub-physiological ionic strength conditions (e.g. <150 mM NaCl).

Polypeptides. The 33-mer and 27-mer polypeptides were synthesized by conventional Fmoc (N-(9-fluoreny) methoxycarbonyl) chemistry as described elsewhere (Mann et al., *J. Biol. Chem.* 269: 23661–7 (1994)). The 33-mer polypeptide (GRRRRSVQWCAVSQPEATKCFQWQRNMRKVRGP) SEQ ID NO: corresponding to the first 33 residues at the N-terminus of human lactoferrin is designated as LF-33 (MW 4,004). The 27-mer polypeptide, LF-27 (MW 3,276), corresponds to LF-33 lacking its N-terminal 6 residues. Phe 26-mer, representing residues Gly-1 through Met-27 was generated by cleaving the last 6 residues of the 33-mer by standard cyanogen bromide cleavage which cleaves polypeptides C-terminal to methionine residues. Polymyxin B (MW 1066, Sigma, St. Louis, Mo.), an anti-endotoxin polypeptide (Cooperstock, M. S., *Antimicrob. Agents Chemother.* 6: 422–425 (1974)), is used as a reference for comparison throughout this study.

LPS. Control standard endotoxins from *Escherichia coli* O113:H10 and *Salmonella abortus* equi (Associates of Cape Cod, Inc, Woods Hole, Mass.) had a potency of 10 endotoxin units (EU) per ng. LPS (purity >99%) from *Neisseria meningitidis* was prepared from the group B strain #6275 and its potency was 25 EU/ng. Lipid A from *E. coli* K12 (List Biological Laboratories, Inc, Campbell, Calif.) had a potency of 8.6 EU/ng. The potency of the LPS from *Pseudomonas aeruginosa* (Sigma) was 0.12 EU/ng. The potency of the above endotoxin was determined with the Limulus enzyme-linked immunosorbent assay (ELISA, 43) in comparison with US Pharmacopeia reference standard endotoxin EC-5.

Limulus ELISA for Determining the 50% Endotoxin-neutralizing Concentration ($ENC_{50}$) of Anti-endotoxin Agents Briefly, 25 µl endotoxin solution (200 EU/ml) was mixed with an equal volume of test materials in a series of two-fold dilution in 0.15 M NaCl in a sterile 96-well tissue culture plate (Nunc A/S, Roskilde, Denmark), and incubated at 37° C. for 1 h in a dry-air incubator. The reaction mixtures were diluted 1000-fold with endotoxin-free water. The endotoxin activity was then quantified with the use of Limulus ELISA (Zhang et al., *J. Clin. Microbiol.* 32: 416–422 (1994)). In Limulus ELISA, endotoxin activated the LAL coagulation at concentrations below one pg or 0.01 endotoxin unit (EU) per ml (Zhang et al., *J. Clin. Microbiol.* 32: 416–422 (1994)). The high sensitivity of the assay allowed for very low levels of the endotoxin activity to be detected. Following incubation of endotoxin with test materials 1000-fold dilution was introduced to eliminate any potential effects of the test materials on the LAL enzyme system. Neither serum nor any of these materials interfered with the enzymatic cascade of the LAL assay itself after a 1000-fold dilution from their highest concentrations used in this study. For each assay, the LAL-endotoxin reaction was carried out at the optimal condition with a linear relationship between the concentration of endotoxin and the optical density at 490 nm ($OD_{490}$). A sigmoid curve was usually obtained between $OD_{490}$ and the logarithmic concentration of an anti-endotoxin agent. The concentration corresponding to the midpoint of the curve was designated as $ENC_{50}$.

Endotoxin induced TNF-α secretion by RAW 264.7 cells. The murine macrophage cell line RAW 264.7 was obtained from the American Type Culture Collection (ATCC, Rockville, Md.) and maintained as described previously (Jeremy, B., *Immunol. Today.* 16: 417–419 (1995)). The concentration of endotoxin in all buffers and media was controlled to below 0.1 EU/ml. The following protocol was essentially described before and used here with minor modifications (Kelly et al., *Infect. Immun.* 59: 4491–6 (1991)). Each well of a 96-well tissue culture plate was seeded with 150 µl RAW 264.7 cells at $10^6$ cells per ml DMEM (Life Technologies, Gaithersburg, Md.) supplemented with 10% heat-treated fetal bovine serum (Life Technologies), 25 mM HEPES (N-2-hydroxyethylpiperazine-N'-2-ethanesulfonic acid; pH 7.3), penicillin (60 U/ml) and streptomycin (60 µg/ml). After overnight incubation at 37° C. in a 6% $CO_2$ incubator, the medium was aspirated and cells washed with 3-changes of endotoxin-free Hank's balanced salt solution (HBSS, Life Technologies) supplemented with 25 mM HEPES (pH 7.3). Control endotoxin (10 ng/ml) and test materials were prepared in HBSS-HEPES. After incubation in a 37° C. water bath for 1 h, 0.2 ml of these solutions was added in triplicate to each well and incubated at 37° C. for 6 h. The supernatants were then collected and stored at −70° C. before the measurement of TNF-60 activity. Controls included HBSS-HEPES and test materials in the absence of endotoxin. TNF-α activity of the medium and test materials was below 160 µg/ml. The human serum used in some experiments was a pool from normal donors.

Determination of TNF activity. TNF-α activity in the culture supernatant was determined based on its cytotoxicity for the mouse fibrosarcoma cell line WEHI 164 cells (ATCC). This cell line was observed to be 4-fold more sensitive to TNF-α than the commonly used L929 fibroblast cells, and the sensitivity was further increased 5-fold by inclusion of actinomycin D (Life Technologies) in the medium (M. R. Ruff and G. E. Gifford, Lymphokines 2: 235–272 (1981). In this assay, the concentration of active TNF-α was correlated with cell death resulting from exposure to TNF-α. Cell death was measured colorimetrically with the viable dye MTT (3-(4,5-dimethylthiazol-2-yl)-2,5-diphenyltetrazolium bromide) method (Mosmann, T., J. Immunol. Methods 65: 55–63 (1983)). The specificity of the assay was verified by using the rabbit anti-mouse TNF-α antibody (Genzyme, Inc., MA). The antibody at 1:100 dilution completely eliminated the cytotoxicity in the culture supernatant of the RAW 264.7 cell stimulated by endotoxin and in the mouse sera collected 1 h after intraperitoneal injection of endotoxin.

Briefly, the 96-well tissue culture plates were seeded with 100 µl WEHI164 cells ($5 \times 10^4$ cells) in RPMI-1640 medium (Life Technologies) containing 10% heat-treated fetal bovine serum, 25 mM HEPES (pH 7.3), penicillin (60 U/ml), streptomycin (60 µg/ml), and actinomycin D (4 µg/ml). After a 2-h incubation at 37° C. in a 6% $CO_2$ incubator, 10 µl twofold serially diluted samples (culture supernatants) or standards (murine recombinant TNF-α, Genzyme) was added to each well, and incubated for 20 h. Cell viability was then determined by the addition of 10 µl MTT (Thiazolyl blue, Sigma) stock solution (5 mg/ml in saline) to each well, and the incubation was allowed to continue for 6 h. 180 µl of acid-isopropanol (containing 40 mM HCl) was added to dissolve the generated dark blue crystals. The plate was read at 570 nm with a reference of 630 nm in a microplate reader. The amount of TNF-α that led to 50% killing of the seeded cells was defined as one unit, equivalent to approximately 15 pg of recombinant TNF-α under the present condition. A standard curve was obtained by incubating known amounts of the recombinant TNF-α with the WEHI cells.

To exclude any potential cytotoxicity of LF-33, the above procedure was followed except that WEHI164 cells were replaced by RAW264.7 cells and the concentration of cells seeded in each well was $1.5 \times 10^5$ cells per 150 µl medium to mimic the condition in the stimulation experiment. At the highest concentration of LF-33 (10 µM) used in this study, no cytotoxicity to RAW264.7 cells was detected.

Galactosamine-sensitized mouse model. i.p. injection of 125 ng E. coli LPS together with 15 mg galactosamine hydrochloride (Sigma) in 0.5 ml 0.15 M NaCl induced nearly 100% lethality in 8- to 10-week-old female NIH/Swiss mice (body weight 20–25 g/mouse). LF-33 was either injected i.v. through tail veins 10 min after the i.p. injection of the LPS-galactosamine mixture or co-injected i.p. with LPS and galactosamine. Lethality was observed for 72 h after injection. In experiments involving measurement of serum TNF-α level, blood samples were collected in serum separator tubes (Becton Dickinson, Rutherford, N.J.) 60–90 min post-injection, and sera were obtained after centrifugation. Serum TNF-α level was measured by the cytotoxic assay described above. Serum TNF-α peak level was found between 60 and 90 min after i.p. injection of LPS.

Statistics. All endotoxin and TNF-α measurements were performed in triplicate in each experiment. At least two independent experiments were performed for each datum. Values are given as mean +/− SD, and were compared by using the unpaired Student's t test. Lethality is compared using the Fisher's exact test.

Generation of galactosamine-sensitized, leukopenic mouse model system. CF-1 mice were rendered immunocompromised by cyclophosphamide treatment three days prior to galactosamine-sensitizing them to the lethal effects of injection with an $LD_{90}$ dose of E. coli 0111 (Bucklin et al., J. Infect. Dis. 174: 1249–1254 (1996)). Under these conditions, circulating leukocytes were reduced by 85% and the $LD_{90}$ was determined to be $5 \times 10^3$ CFU E. coli.

---

---

What is claimed is:

1. An isolated anti-microbial and/or endotoxin-neutralizing polypeptide excluding the polypeptide of SEQ ID NO: 1, consisting of from N-terminus to C-terminus:

(a) a first cluster of 2–7 amino acids wherein 2 of the 2–7 residues are strongly basic and identical to a contiguous sequence contained in the sequence GRRRRS (SEQ ID NO: 4) or a strongly basic substitute of the contiguous sequence;

(b) a second cluster of 17–21 amino acids that has a grand hydropathicity value of at least −0.609 and an average aliphatic index value of at least 35.45;

(c) a third cluster of 2 to 7 amino acids wherein 2 of the 2–7 residues are strongly basic and identical to a contiguous sequence contained in the sequence MRKVRG (SEQ ID NO: 5) or a strongly basic substitute of the contiguous sequence; and optionally (d) a fourth cluster of amino acids that is an endocytosis clearance fragment recognized and internalized by cells via endocytosis clearance pathway or a 1–17 amino acid cluster that contains substitute of a contiguous sequence contained in PVSCIKRDSPIQCIQAIA (SEQ ID NO: 3);

wherein the clusters of amino acids are joined to form a single contiguous amide linkage backbone, and wherein the substitute preserves anti-microbial and/or endotoxin-neutralizing activity of the isolated polypeptide.

2. The isolated polypeptide of claim 1, wherein the optional fourth cluster of 1–17 amino acids has a grand average hydropathicity value of at least 0.174 and an average aliphatic index value of at least 97.14.

3. An isolated anti-microbial and/or endotoxin-neutralizing polypeptide excluding the polypeptide of SEQ ID NO: 1, consisting of from N-terminus to C-terminus:
   (a) a first cluster of 2–7 amino acids wherein 2 of the 2–7 residues are strongly basic and identical to a contiguous sequence contained in the sequence GRRRRS (SEQ ID NO: 4) or a strongly basic substitute of the contiguous sequence;
   (b) a second cluster of 17–21 amino acids that is identical to a contiguous sequence contained in the sequence VQWCAVSQPEATKCFQWQRN;
   (c) a third cluster of 2 to 7 amino acids wherein 2 of the 2–7 residues are strongly basic and identical to a contiguous sequence contained in the sequence MRKVRG (SEQ ID NO: 5) or a strongly basic substitute of the contiguous sequence; and optionally
   (d) a fourth cluster of amino acids that is an endocytosis clearance fragment recognized and internalized by cells via endocytosis clearance pathway or a 1–17 amino acid cluster that contains substitute of a contiguous sequence contained in PVSCIKRDSPIQCIQAIA (SEQ ID NO: 3);
   wherein the clusters of amino acids are joined to form a single contiguous amide linkage backbone, and wherein the substitute preserves anti-microbial and/or endotoxin-neutralizing activity of the isolated polypeptide.

4. The isolated polypeptide of claim 3, which is further characterized by the ability to inhibit microbial growth at a physiological ionic strength with a minimal inhibitory concentration of about 1 to 5 uM.

5. The isolated polypeptide of claim 3, wherein the first cluster is the sequence shown in SEQ ID NO: 4 or a truncation thereof, which retains at least two arginine residues (RR).

6. The isolated polypeptide of claim 3, wherein the third cluster is MRKVRG (SEQ ID NO: 5).

7. The isolated polypeptide of claim 3, wherein the fourth cluster is PVSCIKRDSPIQCIQAI (SEQ ID NO: 7).

8. The isolated polypeptide of claim 3, wherein the polypeptide is a substitute of the sequence shown in SEQ ID NO:2 having a basic residue substitution at positions 2, 3, 4, 5, 28, 29, 31, 39 and 40: a hydrophobic residue substitution at position 7, 9, 10, 11, 12, 17, 18, 20, 21, 23, 32, 35, 37, 38, 44, 46, 47, 49, and 50; and an acidic residue substitution at position 16 and 41.

9. The isolated polypeptide of claim 3, consisting of clusters 1 through 3.

10. The isolated polypeptide of claim 3, consisting of clusters 1 through 4.

11. The isolated polypeptide of claim 3, consisting of:
   (a) a first cluster of 2–7 amino acids wherein 2 of the 2–7 residues are strongly basic and identical to a contiguous sequence contained in the sequence GRRRRS (SEQ ID NO: 4);
   (b) a second cluster of 17–21 amino acids that has a grand hydropathicity value of at least –0.609 and an average aliphatic index value of at least 35.45;
   (c) a third cluster of 2 to 7 amino acids wherein 2 of the 2–7 residues are strongly basic and identical to a contiguous sequence contained in the sequence MRKVRG (SEQ ID NO: 5); and optionally
   (d) a fourth cluster of amino acids that is an endocytosis clearance fragment recognized and internalized by cells via endocytosis clearance pathway or a 1–17 amino acid cluster that contains substitute of a contiguous sequence contained in PVSCIKRDSPIQCIQAIA (SEQ ID NO: 3);
   wherein the clusters of amino acids are joined to from a single contiguous amide linkage backbone; and wherein the substitute preserves anti-microbial and/or endotoxin-neutralizing activity of the isolated polypeptide.

12. An isolated polypeptide which has a neutral charge amino acid substituted for the glutamate (E) 16 in SEQ ID NO: 2.

13. The isolated polypeptide of claim 12, wherein the neutral charge amino acid is alanine.

14. The isolated polypeptide of claim 12, wherein the neutral charge amino acid is glycine.

15. The isolated polypeptide of claim 12, wherein the neutral charge amino acid is valine.

16. A pharmaceutical composition comprising a pharmaceutically acceptable carrier and an isolated anti-microbial and/or endotoxin-neutralizing polypeptide that consists of:
   (a) a first cluster of 2–7 amino acids wherein 2 of the 2–7 residues are strongly basic;
   (b) a second cluster of 17–21 amino acids that has a grand hydropathicity value of at least –0.609 and an average aliphatic index value of at least 35.45;
   (c) a third cluster of 2 to 7 amino acids wherein 2 of the 2–7 residues are strongly basic; and optionally
   (d) a fourth cluster of amino acids that is an endocytosis clearance fragment recognized and internalized by cells via endocytosis clearance pathway or a 1–17 amino acid cluster that has a grand average hydropathicity value of at least 0.174 and an average aliphatic index value of at least 97.14.

17. A pharmaceutical composition comprising a pharmaceutically acceptable carrier and an isolated polypeptide that consists of:
   (a) a first cluster of 2–7 amino acids wherein 2 of the 2–7 residues are strongly basic and identical to a contiguous sequence contained in the sequence GRRRRS (SEQ ID NO: 4) or a strongly basic substitute of the contiguous sequence;
   (b) a second cluster of 17–21 amino acids that has a grand hydropathicity value of at least –0.609 and an average aliphatic index value of at least 35.45;
   (c) a third cluster of 2 to 7 amino acids wherein 2 of the 2–7 residues are strongly basic and identical to a contiguous sequence contained in the sequence MRKVRG (SEQ ID NO: 5) or a strongly basic substitute of the contiguous sequence; and optionally
   (d) a fourth cluster of amino acids that is an endocytosis clearance fragment recognized and internalized by cells via endocytosis clearance pathway or a 1–17 amino acid cluster that contains substitute of a contiguous sequence contained in PVSCIKRDSPIQCIQAIA (SEQ ID NO: 3);
   wherein the substitute preserves anti-microbial and/or endotoxin-neutralizing activity of the isolated polypeptide.

* * * * *

SEQUENCE LISTING

<160> NUMBER OF SEQ ID NOS: 1

<210> SEQ ID NO 1
<211> LENGTH: 17
<212> TYPE: PRT
<213> ORGANISM: Homo sapiens

<400> SEQUENCE: 1

Pro Val Ser Cys Ile Lys Arg Asp Ser Pro Ile Gln Cys Ile Gln Ala Ile
1               5                   10                  15